US011393983B2

(12) United States Patent
Huang et al.

(10) Patent No.: US 11,393,983 B2
(45) Date of Patent: Jul. 19, 2022

(54) PHENYL BIPHENYLPYRIMIDINE COMPOUND AND AN ORGANIC ELECTROLUMINESCENT DEVICE USING THE SAME

(71) Applicant: E-RAY OPTOELECTRONICS TECHNOLOGY CO., LTD., Taoyuan (TW)

(72) Inventors: Heh-Lung Huang, Taoyuan (TW); Teng-Chih Chao, Taoyuan (TW); Po-Wei Hsu, Taoyuan (TW); Yi-Huan Fu, Taoyuan (TW); Chi-Jen Lin, Taoyuan (TW)

(73) Assignee: E-RAY OPTOELECTRONICS TECHNOLOGY CO., LTD., Taoyuan (TW)

( * ) Notice: Subject to any disclaimer, the term of this patent is extended or adjusted under 35 U.S.C. 154(b) by 350 days.

(21) Appl. No.: 16/585,049

(22) Filed: Sep. 27, 2019

(65) Prior Publication Data

US 2020/0127211 A1 Apr. 23, 2020

(30) Foreign Application Priority Data

Oct. 23, 2018 (TW) .................................. 107137368

(51) Int. Cl.
*C07D 239/26* (2006.01)
*H01L 51/00* (2006.01)
(Continued)

(52) U.S. Cl.
CPC ........ *H01L 51/0067* (2013.01); *C07D 239/26* (2013.01); *C07D 401/04* (2013.01); *H01L 51/5072* (2013.01); *H01L 51/5096* (2013.01)

(58) Field of Classification Search
None
See application file for complete search history.

(56) References Cited

U.S. PATENT DOCUMENTS

| 4,769,292 A | 9/1988 | Tang et al. |
| 5,707,745 A | 1/1998 | Forrest et al. |

(Continued)

FOREIGN PATENT DOCUMENTS

| CN | 107021926 A | * 8/2017 | ........... C07D 221/20 |
| TW | I582081 | 5/2017 | |

(Continued)

OTHER PUBLICATIONS

Machine translation of WO-2017188596, translation generated Oct. 2021, 29 pages. (Year: 2021).*

(Continued)

*Primary Examiner* — Robert S Loewe
(74) *Attorney, Agent, or Firm* — Amin, Turocy & Watson, LLP

(57) ABSTRACT

The present disclosure provides phenyl biphenylpyrimidine compounds of formula (I) and an organic electroluminescent device using the same:

(Continued)

(51) Int. Cl.
*C07D 401/04* (2006.01)
*H01L 51/50* (2006.01)

(56) References Cited

U.S. PATENT DOCUMENTS

| | | | |
|---|---|---|---|
| 5,844,363 A | 12/1998 | Gu et al. | |
| 6,465,115 B2 | 10/2002 | Shi et al. | |
| 6,596,415 B2 | 7/2003 | Shi et al. | |
| 2016/0380208 A1* | 12/2016 | La | C09K 11/025 257/40 |
| 2017/0133602 A1* | 5/2017 | Lee | C09K 11/02 |
| 2018/0141933 A1* | 5/2018 | Ha | C07D 409/10 |
| 2018/0337341 A1* | 11/2018 | Heo | H01L 51/50 |

FOREIGN PATENT DOCUMENTS

| | | | |
|---|---|---|---|
| WO | WO-2017171420 A1 * | 10/2017 | C07D 251/24 |
| WO | WO-2017188596 A1 * | 11/2017 | C07D 251/24 |

OTHER PUBLICATIONS

Machine translation of WO-2017171420, translation generated Oct. 2021, 29 pages. (Year: 2021).*
Machine translation of CN-107021926, translation generated Oct. 2021, 22 pages (Year: 2021).*

* cited by examiner

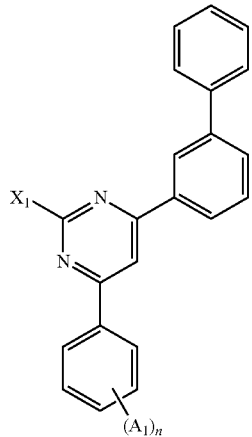

(I)

wherein X1 and A1 each independently represents substituted or unsubstituted C6-30 aryl or substituted or unsubstituted C5-30 heteroaryl having at least one heteroatom selected from the group consisting of N, O, and S, and n represents an integer of 1 or 2.

13 Claims, 3 Drawing Sheets

PHENYL BIPHENYLPYRIMIDINE COMPOUND AND AN ORGANIC ELECTROLUMINESCENT DEVICE USING THE SAME

TECHNICAL FIELD

The present disclosure relates to a material for an organic electroluminescent device and an organic electroluminescent device using the material.

BACKGROUND

Recently, the organic electroluminescent device (OLED) has commercial attraction for a high-luminance high-density pixel display because of its long life, high efficiency, low driving voltage, wide color gamut, and low cost. In order to satisfy the application of the organic electroluminescent device of the organic electroluminescent device, particular emphasis is placed on the development of its novel organic materials.

A typical OLED is sandwiched between at least one organic emissive layer between an anode and a cathode. When a current is applied to an OELD, the anode injects holes, and the cathode injects electrons into one or more organic emission layers, and the injected holes and electrons each migrate to the opposite charged electrode. When electrons and holes are confined to the same molecule, an "exciton" is formed, which has a localized electron-hole pair excited by an excited energy state, and the exciton is relaxed by the illuminating mechanism to emit light. In order to improve the charge transport capability and luminous efficiency of the devices, one or more additional layers are bonded adjacent to the light emitting layer, such as the electron transport layer and/or the hole transport layer, or the electron blocking layer and/or the hole blocking layer. In the literature, it has been well documented that the host material is blended with another guest material to enhance device performance and adjust color. Several OLED materials and device configurations are described in U.S. Pat. Nos. 4,769,292, 5,844,363, 5,707,745, 6,596,415, and 6,465,115. E-Ray Optoelectronics Technology has applied for in 2016 and was awarded the TW Patent No. 1582081 in 2017. The electronic transmission materials introduced in this patent have certain novelty and effect, and the effect of this new patent application is better than the previous disclosure.

The reason for manufacturing a multi-layer structure OLED includes a stable interface between the electrodes and the organic layer and a combination of organic materials. In organic materials, the mobility of electrons and holes is significantly different. If the suitable hole transport and electron transport layer are used, holes and electrons can be efficiently transmitted to the emissive layer. The density of the electrons and holes in the emissive layer is balanced to increase luminous efficiency. The proper combination of the above organic layers enhances the efficiency and lifetime of the component. However, it is still difficult to find organic materials that meet the needs of all practical display applications, especially organic materials for vehicle displays or illumination sources, which are required to have high temperature resistance and long life. Most common organic materials are only resistant to the temperature of 100° C.

Therefore, there is a need for an organic material that can significantly improve the lifetime of the organic electroluminescent device and increase the carrier mobility to meet the needs of diverse applications.

SUMMARY

The purpose of the present disclosure is to provide a material for an organic electroluminescent device having a long lifetime, high carrier mobility and high heat resistance.

The present disclosure provides a phenyl biphenylpyrimidine compound of formula (I):

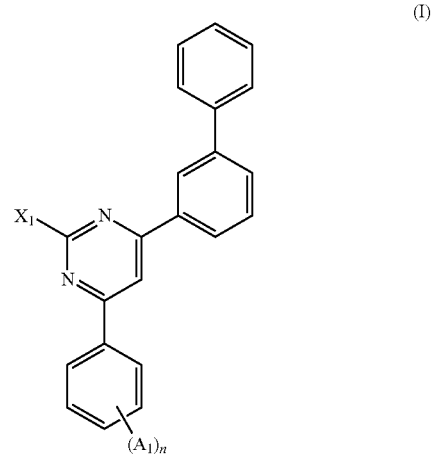

(I)

wherein $X_1$ and $A_1$ are the same or different and each independently represents substituted or unsubstituted $C_{6-30}$ aryl or substituted or unsubstituted $C_{5-30}$ heteroaryl having at least one heteroatom selected from the group consisting of N, O, and S; and n represents an integer of 1 or 2, and when n represents 1 and $A_1$ is an unsubstituted phenyl, the $A_1$ is bonded to a para-position relative to a pyrimidine moiety; when n represents 2, each $A_1$ is the same or different.

In an embodiment of the phenyl biphenylpyrimidine compound of formula (I) of the present disclosure, $X_1$ is one selected from the group consisting of unsubstituted pyridyl, phenyl substituted with halogen, and phenyl substituted with $C_{1-4}$ alkyl. For example, the phenyl biphenylpyrimidine compound of formula (I) is selected from the group consisting of:

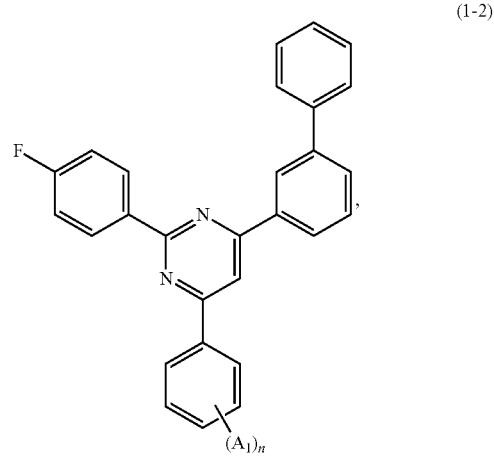

(1-2)

(1-3)

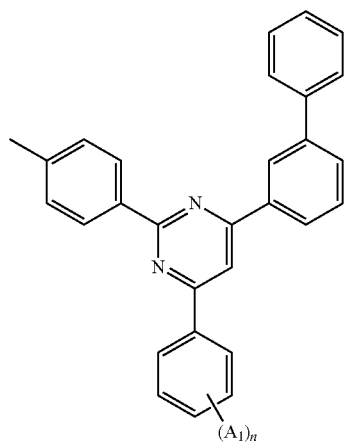

and (1-4)

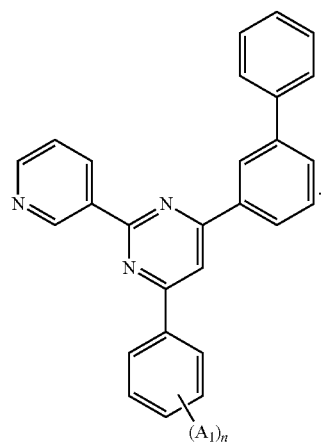

In an embodiment of the phenyl biphenylpyrimidine compound of formula (I) of the present disclosure, $A_1$ is substituted or unsubstituted $C_{9-30}$ fused polycyclic aromatic hydrocarbon, substituted or unsubstituted $C_{9-30}$ aromatic hydrocarbon having a spiro structure, or substituted or unsubstituted $C_{5-30}$ fused polycyclic aromatic hydrocarbon having at least one heteroatom selected from the group consisting of N, O, and S.

More specifically, $A_1$ is one selected from the group consisting of:

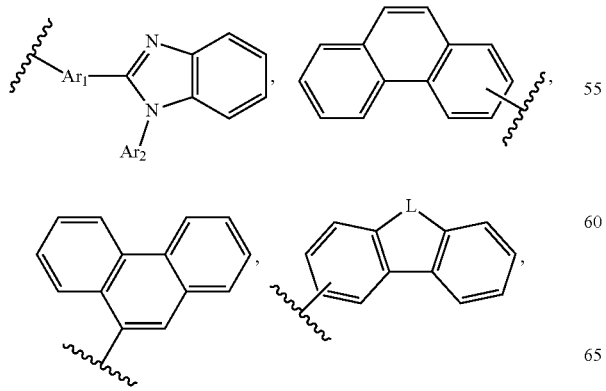

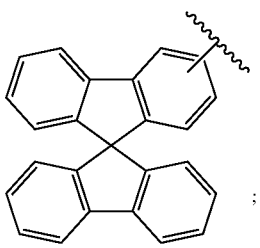

and wherein $Ar_1$ represents unsubstituted $C_{6-18}$ arylene or a single bond attached to the compound of formula (I); $Ar_2$ represents hydrogen or unsubstituted $C_{6-18}$ aryl;

L represents N, N—$R_1$, O or S, and $R_1$ is unsubstituted $C_{6-18}$ aryl; and $L_1$ represents N or N—$R_2$, and $R_2$ is unsubstituted $C_{6-18}$ arylene attached to the compound of formula (I).

In an embodiment of the phenyl biphenylpyrimidine compound of formula (I) of the present disclosure, the compound of the formula (I) is represented by formula (1-5) or formula (1-6) when n is 1:

(1-5)

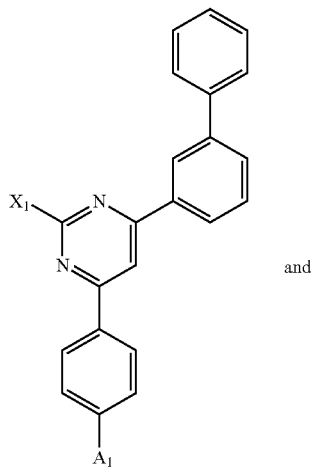

and (1-6)

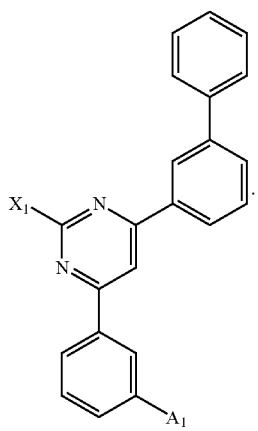

Yet in an embodiment of the phenyl biphenylpyrimidine compound of formula (I) of the present disclosure, the compound is selected from the group consisting of:
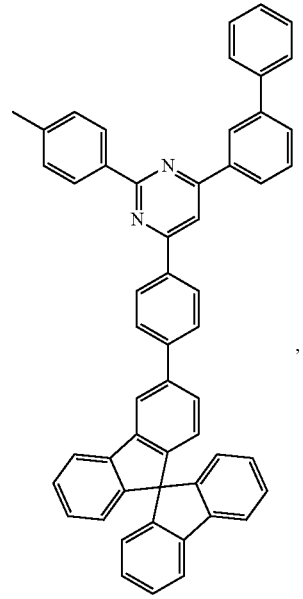
(2-4)
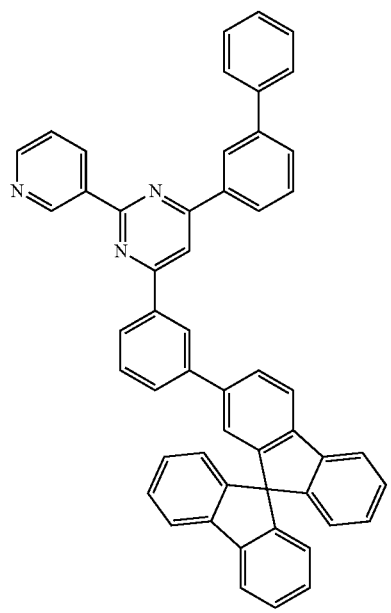
(3-4)
-continued
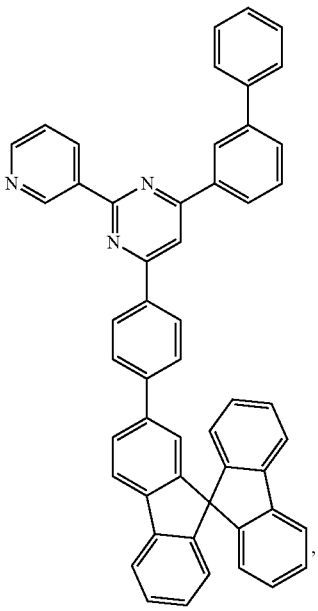
(3-5)
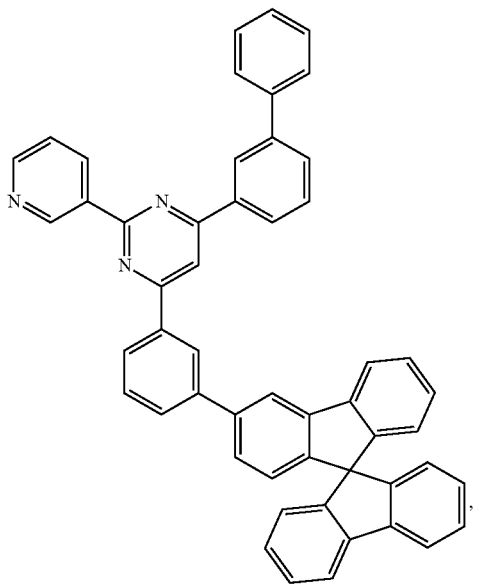
(3-6)

(3-7)

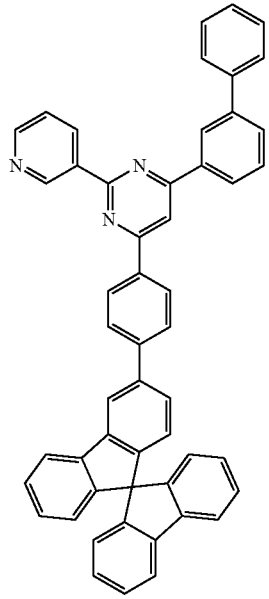

and (3-8)

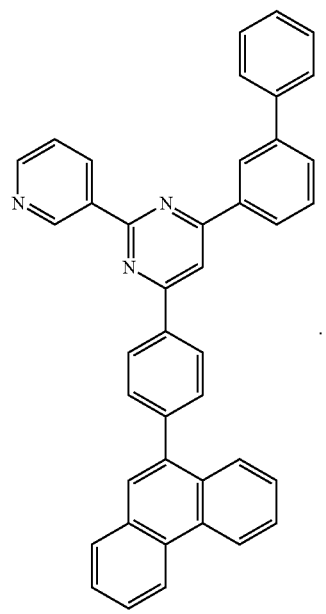

In an embodiment of the phenyl biphenylpyrimidine compound of formula (I) of the present disclosure, the compound of formula (I) is represented by formula (1-7) when n is 2:

(1-7)

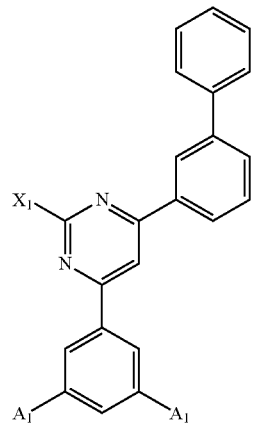

wherein each $A_1$ is the same or different.

The present disclosure further provides the organic electroluminescent device, comprising: a cathode; an anode; and an organic layer. The organic layer is sandwiched between the cathode and the anode, and contains the phenyl biphenylpyrimidine compound of formula (I) of the present disclosure.

In an embodiment of the organic electroluminescent device of the present disclosure, the organic layer is an electron transport layer and has a thickness of 20 nm to 30 nm. In addition, the electron transport layer can further contain an N-type electrically conductive dopant, and the N-type electrically conductive dopant is in an amount of more than 0% by weight up to 50% by weight. For example, the N-type electrically conductive dopant is lithium quinolate.

In an embodiment of the organic electroluminescent device of the present disclosure, the organic layer further comprises a hole blocking layer, and a thickness thereof is more than 0 nm up to 5 nm.

Based on the present disclosure, owing to the phenyl biphenylpyrimidine compound of formula (I) provided by the present disclosure, the bonding position of the biphenyl group and the pyrimidine moiety is more effective than other bonding positions to improve the lifetime of the organic electroluminescent device and improve carrier migration rate, providing the benefits of good heat resistance.

BRIEF DESCRIPTION OF THE DRAWINGS

Embodiments of the present disclosure are illustrated by way of examples with reference to the accompanying drawings.

DETAILED DESCRIPTION OF THE EMBODIMENTS

Figure 1:
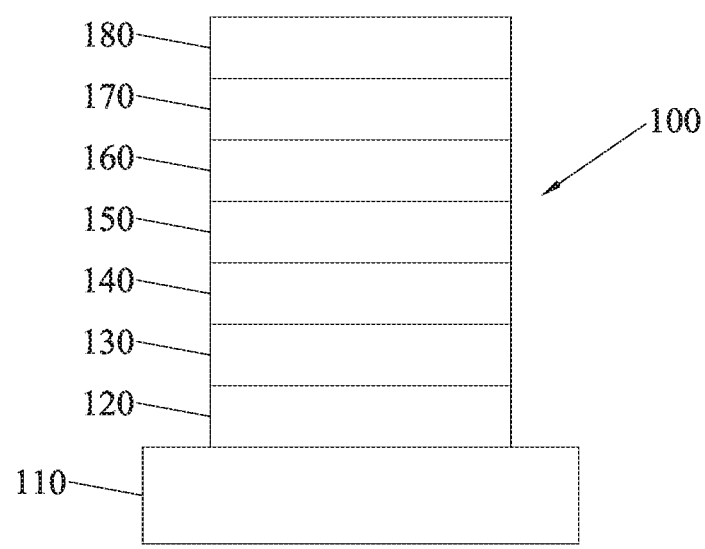
FIG. 1 is a schematic cross-sectional view showing an embodiment of the organic electroluminescent device of the present disclosure.

The embodiments of the present disclosure are described by way of specific examples, and one skilled in the art can readily understand the advantages and functions based on the specification of the present disclosure. The present disclosure may be embodied or applied in various other embodiments. The various details of the present disclosure may be variously modified and changed without departing from the spirit and scope of the disclosure. In addition, all ranges and values herein are inclusive and combinable. Any value or point falling within the ranges recited herein, such as any integer, may be the minimum or maximum value to derive the lower range and the like.

As used herein, a term "substituted" in "substituted or unsubstituted" means that a hydrogen atom in a functional group is replaced by another atom or group (i.e., a substituent). Each of the substituents is independently selected from at least one of the group consisting of: deuterium, halogen, $C_{1-30}$alkyl, $C_{1-30}$alkoxy, $C_{6-30}$aryl, $C_{5-30}$heteroaryl, $C_{5-30}$heteroaryl substituted with $C_{6-30}$aryl, benzimidazolyl, $C_{3-30}$cycloalkyl, $C_{5-7}$heterocycloalkyl, tri-$C_{1-30}$alkylsilyl, tri-$C_{1-30}$arylsilyl, di-$C_{1-30}$alkyl $C_{6-30}$arylsilyl, $C_{1-30}$alkyldi-$C_{6-30}$arylsilyl, $C_{2-30}$alkenyl, $C_{2-30}$alkynyl, cyano, di-$C_{1-30}$alkylamino, di-$C_{6-30}$arylboryl, di-$C_{1-30}$arylboryl, $C_{1-30}$alkyl, $C_{6-30}$aryl$C_{1-30}$alkyl, $C_{1-30}$alkyl$C_{6-30}$ aryl, carboxyl, nitro and hydroxyl.

In an embodiment, the $C_{6-30}$aryl is substituted with at least one substituent selected from the group consisting of halogen, $C_{1-5}$alkyl, $C_{6-30}$aryl and $C_{5-30}$heteroaryl.

In another embodiment, the $C_{6-30}$aryl is substituted with at least one substituent selected from the group consisting of halogen, methyl, phenyl, benzimidazolyl and carbazolyl.

In an embodiment, the $C_{5-30}$heteroaryl group containing at least one heteroatom selected from the group consisting of N, O, and S is substituted with a $C_{6-30}$aryl substituent.

In another embodiment, the $C_{6-30}$aryl is substituted with a phenyl substituent.

The term "aryl" used herein indicates aryl or aryl(ene). The aryl refers to a monocyclic ring or a fused ring derived from an aromatic hydrocarbon, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthryl, phenylphenanthryl, anthracyl, indenyl, triphenylenyl, pyrenyl, naphthacenyl, perylenyl, chrysenyl, napthacenyl, fluoranthenyl, and the like.

The term "heteroaryl" used herein indicates heteroaryl of heteroaryl(ene). The heteroaryl refers to an aryl having a ring main chain atom of at least one heteroatom selected from the group consisting of N, O, and S; and it can be a monocyclic ring or a fused ring formed by combining with at least one benzene ring. The monocyclic ring type includes, for example, furyl, thienyl, pyrryl, imidazolyl, pyrazolyl, thiazolyl, thiadizolyl, isothiazolyl, isoxazolyl, oxazolyl, oxadiazolyl, triazinyl, tetrazinyl, triazolyl, tetrazolyl, furazanyl, pyridyl, pyrazinyl, pyrimidyl, and pyridazinyl. The fused ring type includes, for example, benzofuranyl, benzothienyl, isobenzofuranyl, dibenzofuranyl, dibenzothienyl, benzimidazolyl, benzothiazolyl, benzoisothiazolyl, benzoisoxazolyl, quinolyl, isoquinolyl, cinnolinyl, quinazolyl, quinoxalyl, carbazolyl, phenoxazinyl, phenanthridinyl, benzodioxolyl, and acridanyl.

In embodiments, preferable examples of the phenyl biphenylpyrimidine compound of formula (I) is selected from, but not limited to, the following Table 1.

TABLE 1

| No. | Structure |
|---|---|
| 1-1 | 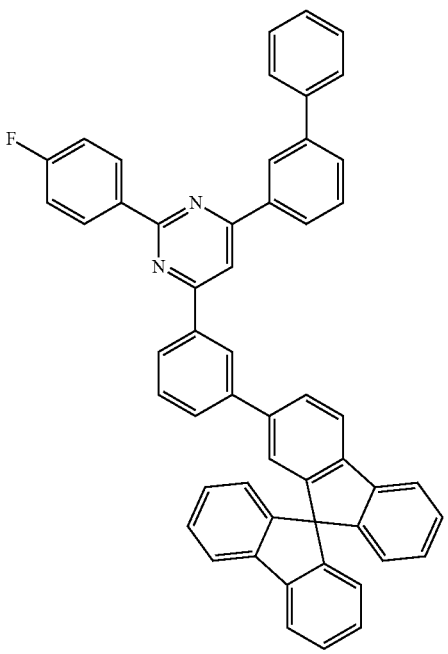 [SMILES: Fc1ccc(-c2nc(-c3cccc(-c4ccccc4)c3)cc(-c3cccc(-c4ccc5c(c4)C4(c6ccccc6-c6ccccc64)c4ccccc4-5)c3)n2)cc1] |
| 1-2 | 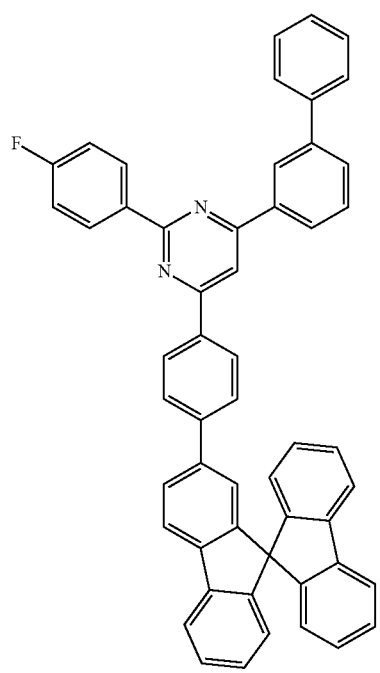 [SMILES: Fc1ccc(-c2nc(-c3ccc(-c4ccc5c(c4)C4(c6ccccc6-c6ccccc64)c4ccccc4-5)cc3)cc(-c3cccc(-c4ccccc4)c3)n2)cc1] |

TABLE 1-continued
| No. | Structure |
|---|---|
| 1-3 | 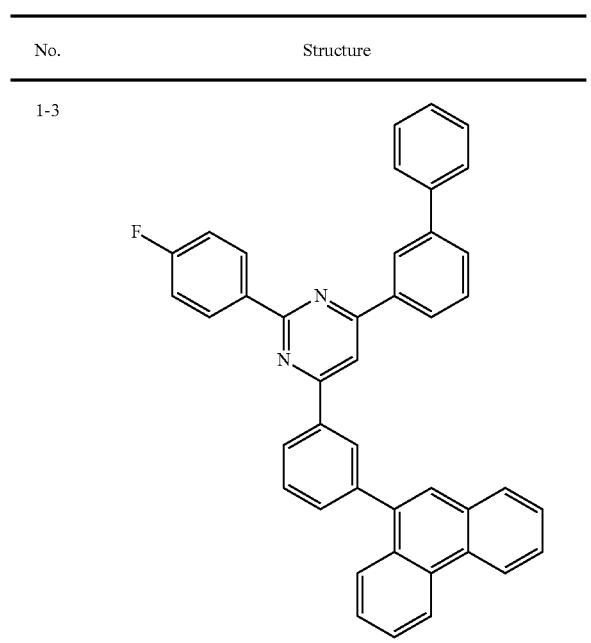 |
| 1-4 | 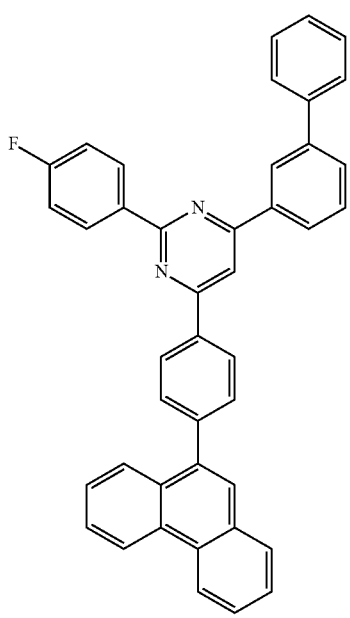 [SMILES: Fc1ccc(-c2nc(-c3ccc(-c4cc5ccccc5c5ccccc45)cc3)cc(-c3cccc(-c4ccccc4)c3)n2)cc1] |
| 1-5 | 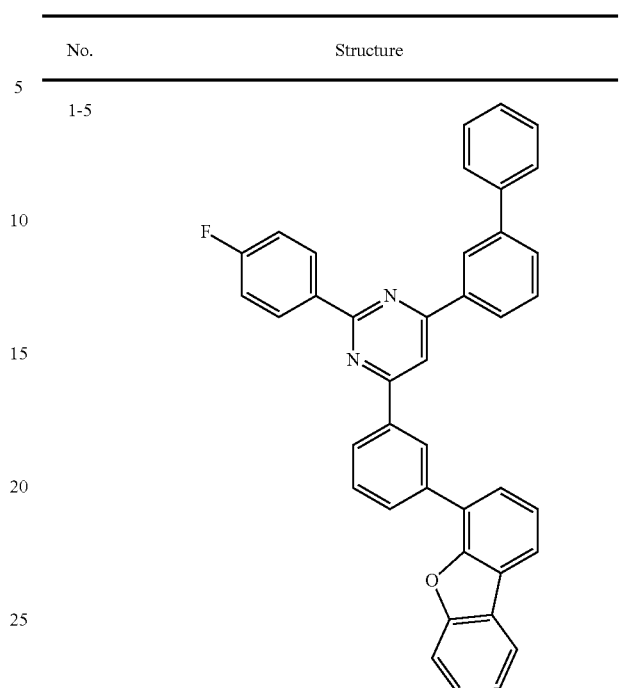 |
| 1-6 | |

TABLE 1-continued
| No. | Structure |
|---|---|
| 1-7 | |
| 1-8 | 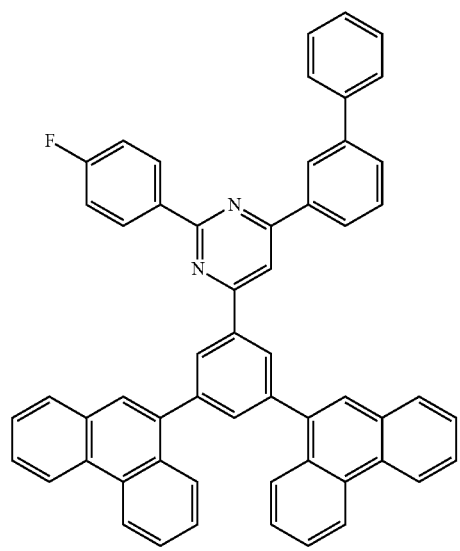 |
| 1-9 | 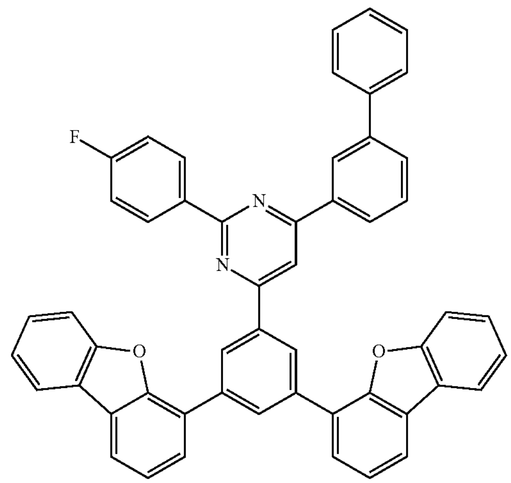 |
| 1-10 | 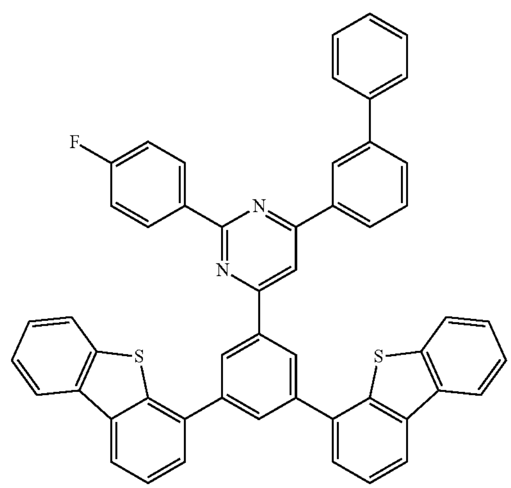 |
| 2-1 | 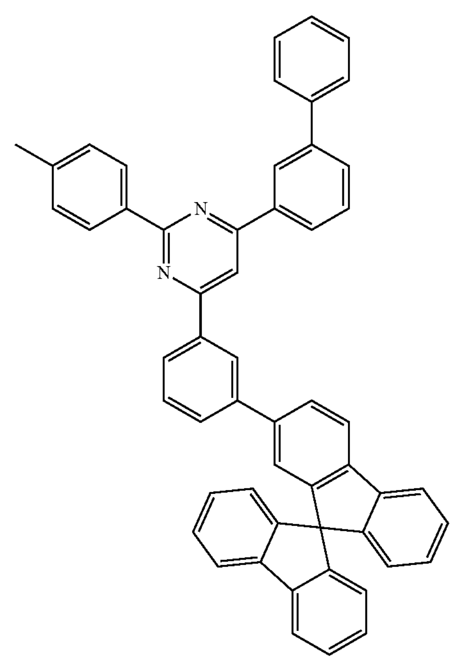 [SMILES: Cc1ccc(-c2nc(-c3cccc(-c4ccccc4)c3)cc(-c3cccc(-c4ccc5c(c4)C4(c6ccccc6-c6ccccc64)c4ccccc4-5)c3)n2)cc1] |

TABLE 1-continued

| No. | Structure |
|-----|-----------|
| 2-2 | 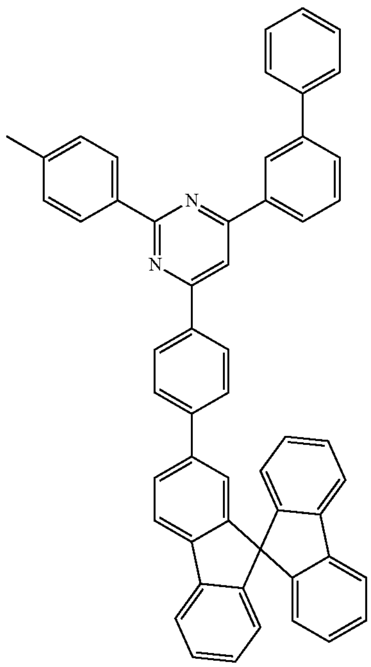 [SMILES: Cc1ccc(-c2nc(-c3ccc(-c4ccc5c(c4)C4(c6ccccc6-c6ccccc64)c4ccccc4-5)cc3)cc(-c3cccc(-c4ccccc4)c3)n2)cc1] |
| 2-3 | 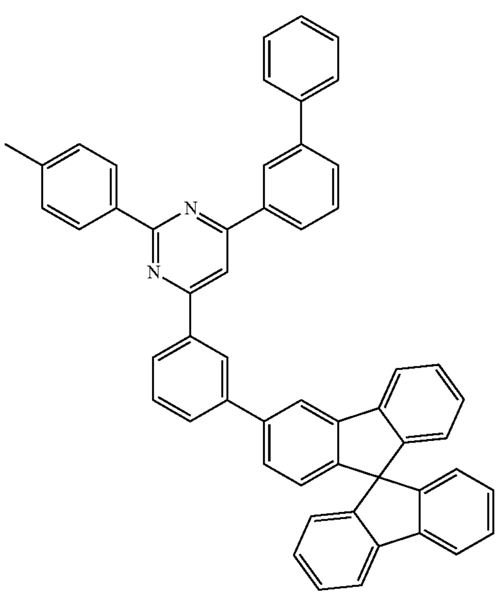 [SMILES: Cc1ccc(-c2nc(-c3cccc(-c4ccccc4)c3)cc(-c3cccc(-c4ccc5c(c4)-c4ccccc4C54c5ccccc5-c5ccccc54)c3)n2)cc1] |
| 2-4 | |
| 2-5 | |

TABLE 1-continued
| No. | Structure |
|---|---|
| 2-6 | 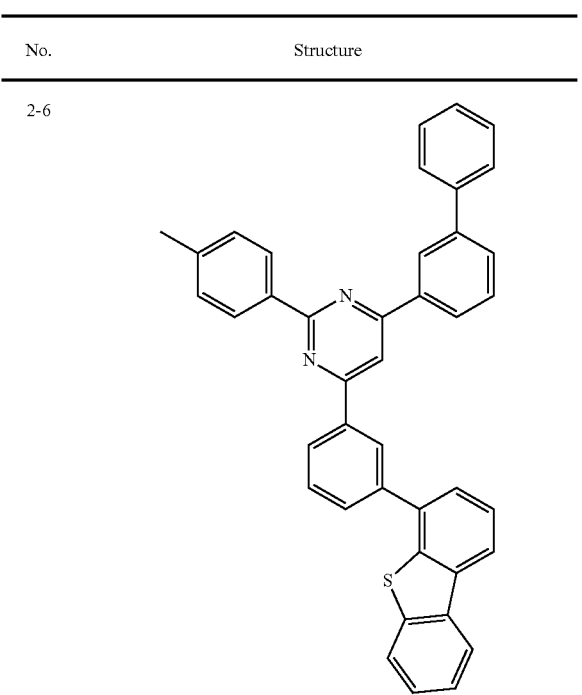 |
| 2-7 | 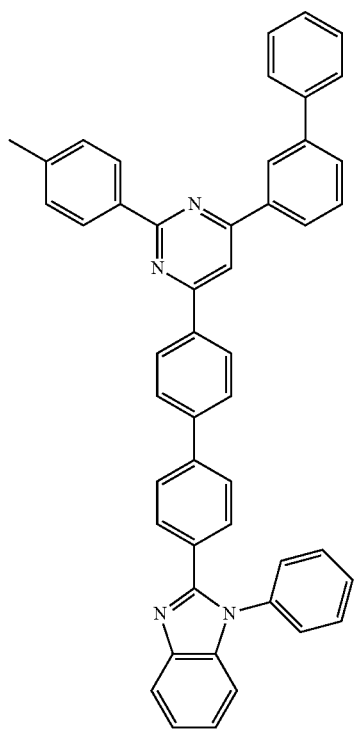 [SMILES: Cc1ccc(-c2nc(-c3ccc(-c4ccc(-c5nc6ccccc6n5-c5ccccc5)cc4)cc3)cc(-c3cccc(-c4ccccc4)c3)n2)cc1] |
| 2-8 | 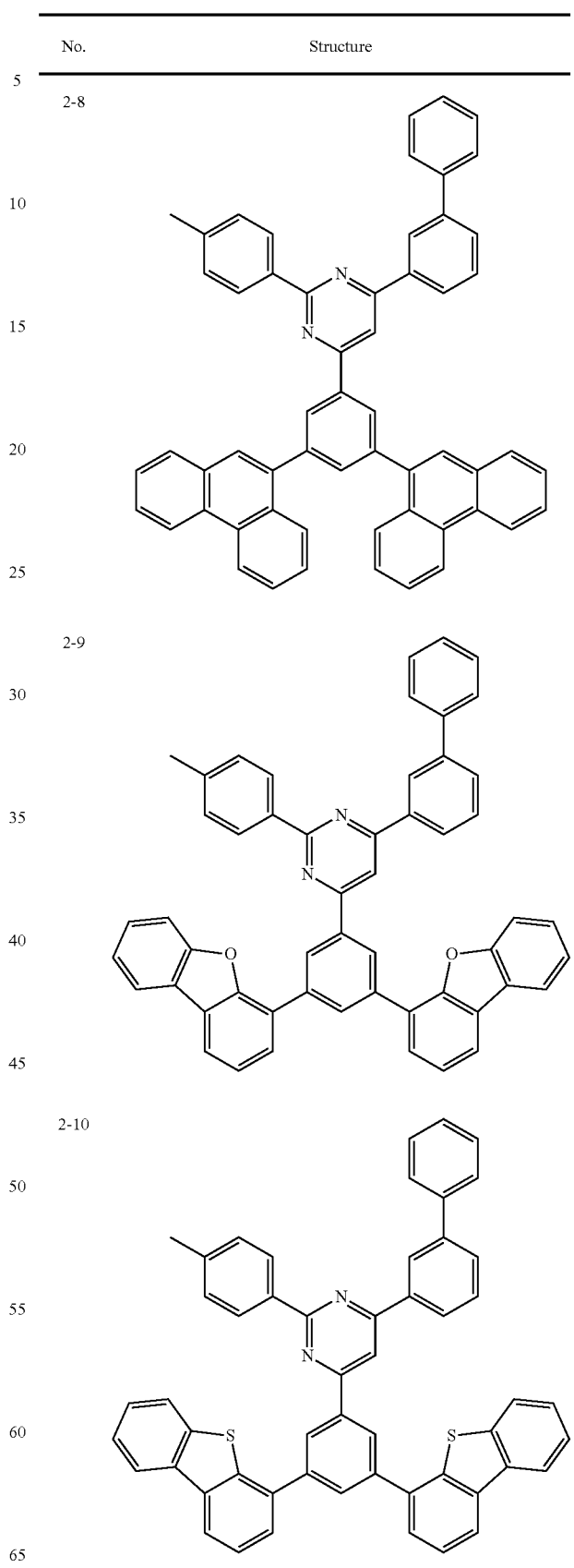 |
| 2-9 | 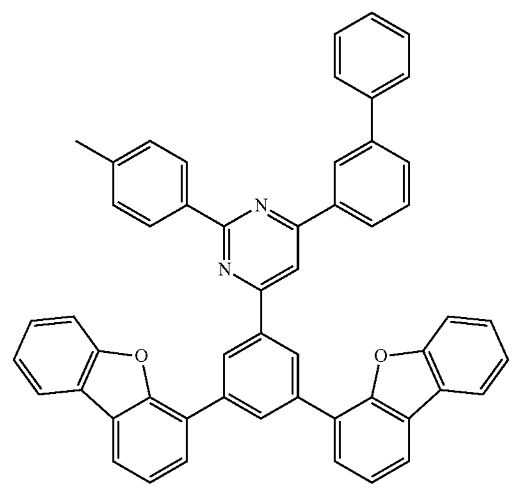 [SMILES: Cc1ccc(-c2nc(-c3cccc(-c4ccccc4)c3)cc(-c3cc(-c4cccc5c4oc4ccccc45)cc(-c4cccc5c4oc4ccccc45)c3)n2)cc1] |
| 2-10 | 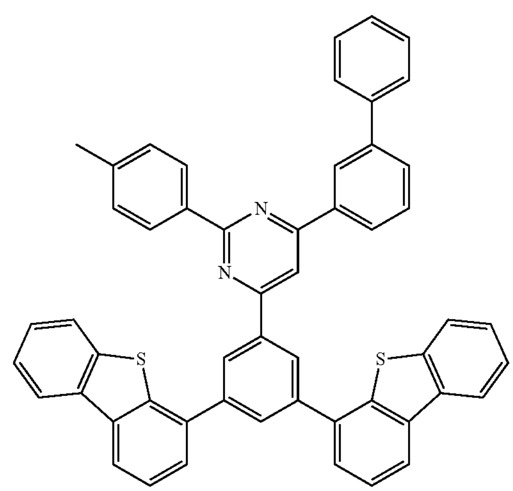 |

TABLE 1-continued
| No. | Structure |
|---|---|
| 3-1 | 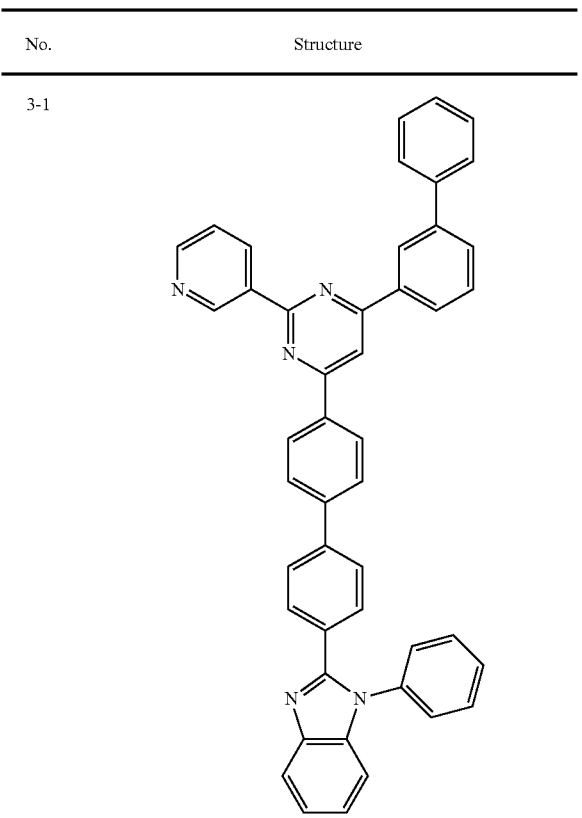 |
| 3-2 | 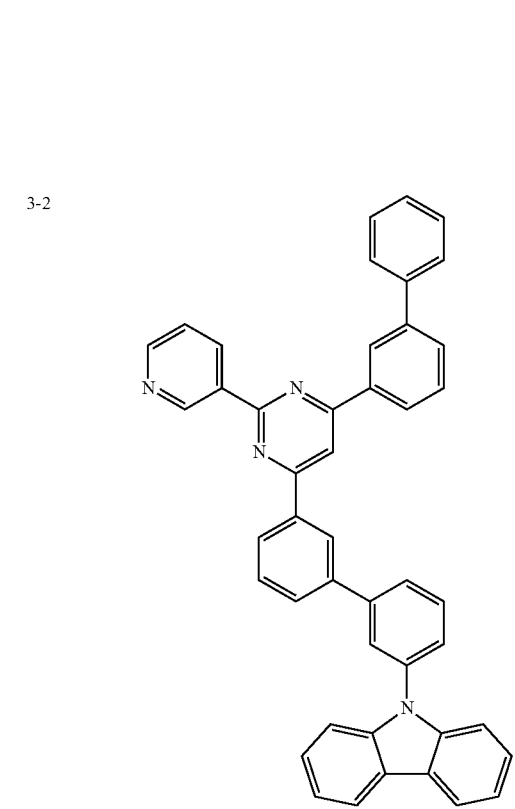 |
| 3-3 | 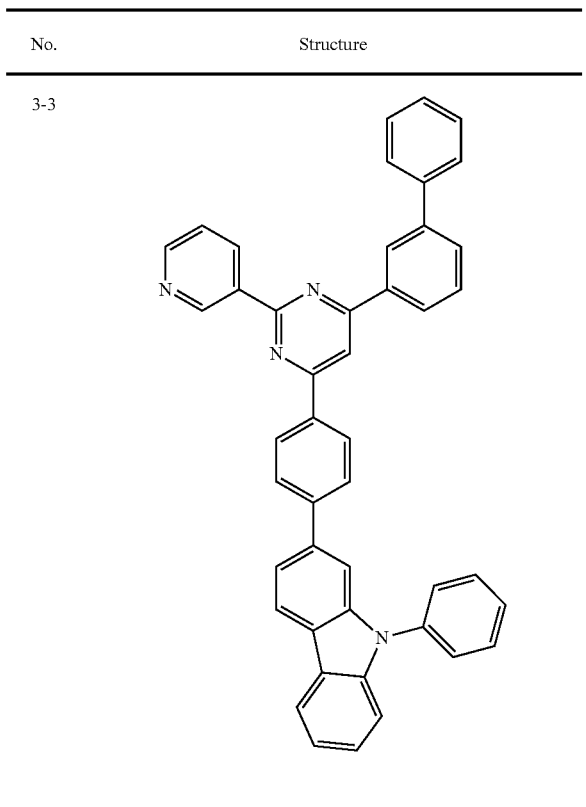 |
| 3-4 | 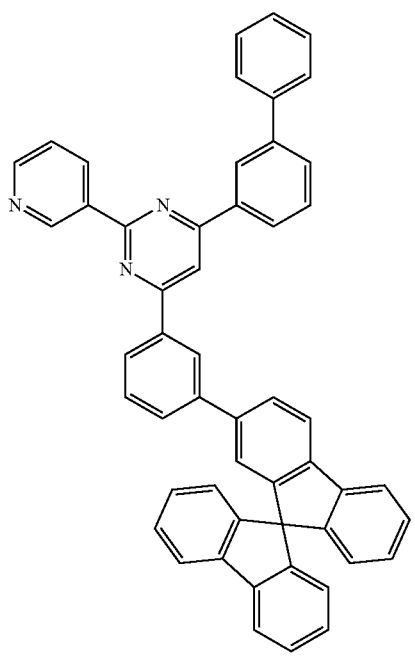 [SMILES: c1ccc(-c2cccc(-c3cc(-c4cccc(-c5ccc6c(c5)C5(c7ccccc7-c7ccccc75)c5ccccc5-6)c4)nc(-c4cccnc4)n3)c2)cc1] |

TABLE 1-continued
| No. | Structure |
|---|---|
| 3-5 | 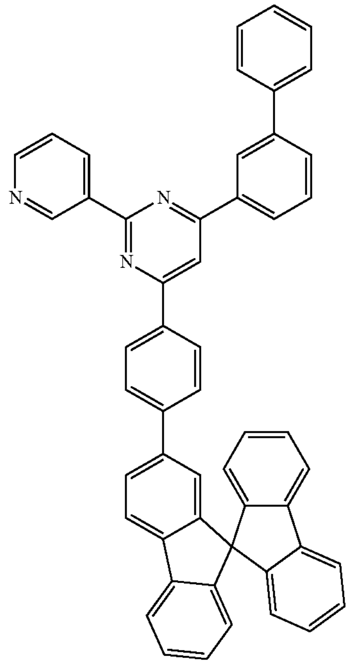 [SMILES: c1ccc(-c2cccc(-c3cc(-c4ccc(-c5ccc6c(c5)C5(c7ccccc7-c7ccccc75)c5ccccc5-6)cc4)nc(-c4cccnc4)n3)c2)cc1] |
| 3-6 | 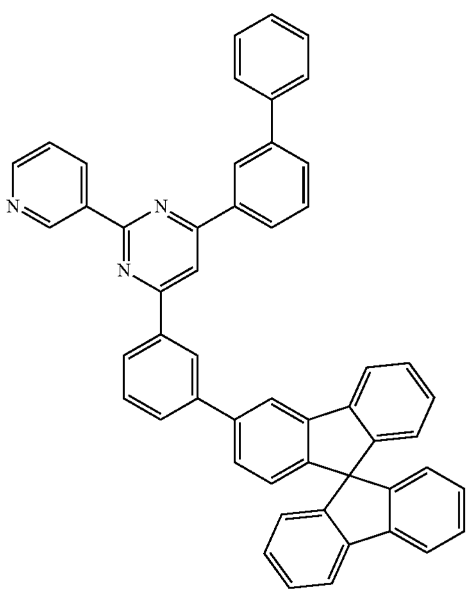 [SMILES: c1ccc(-c2cccc(-c3cc(-c4cccc(-c5ccc6c(c5)-c5ccccc5C65c6ccccc6-c6ccccc65)c4)nc(-c4cccnc4)n3)c2)cc1] |
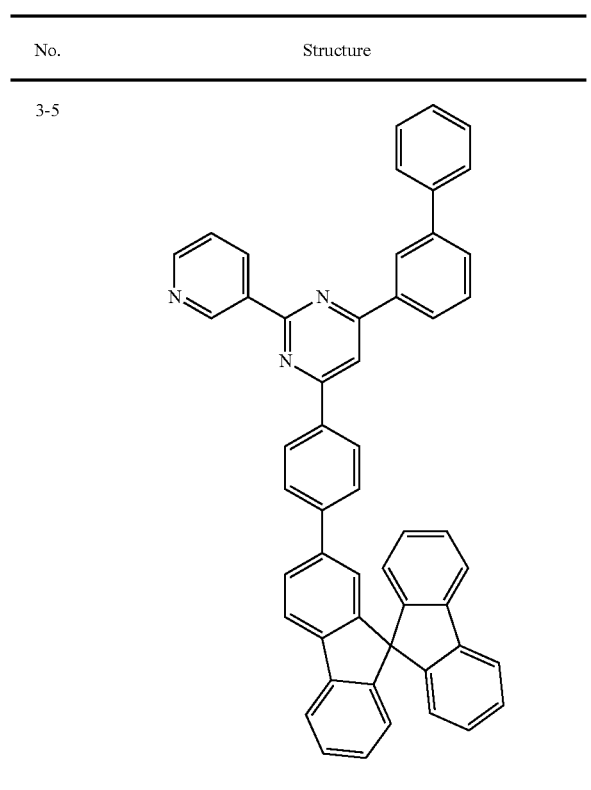
TABLE 1-continued
| No. | Structure |
|---|---|
| 3-7 | 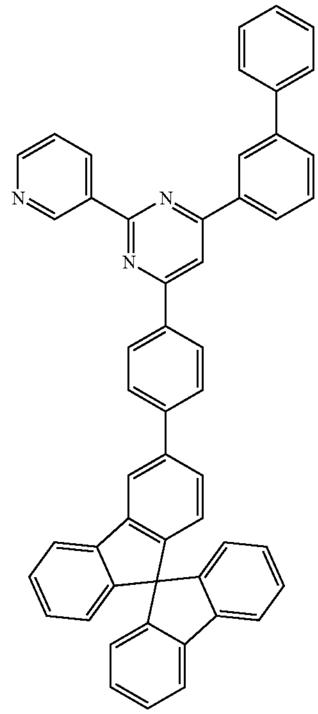 [SMILES: c1ccc(-c2cccc(-c3cc(-c4ccc(-c5ccc6c(c5)-c5ccccc5C65c6ccccc6-c6ccccc65)cc4)nc(-c4cccnc4)n3)c2)cc1] |
| 3-8 | 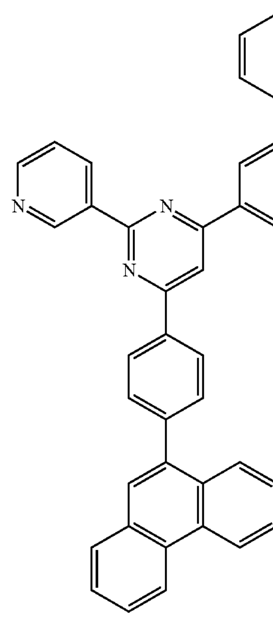 |
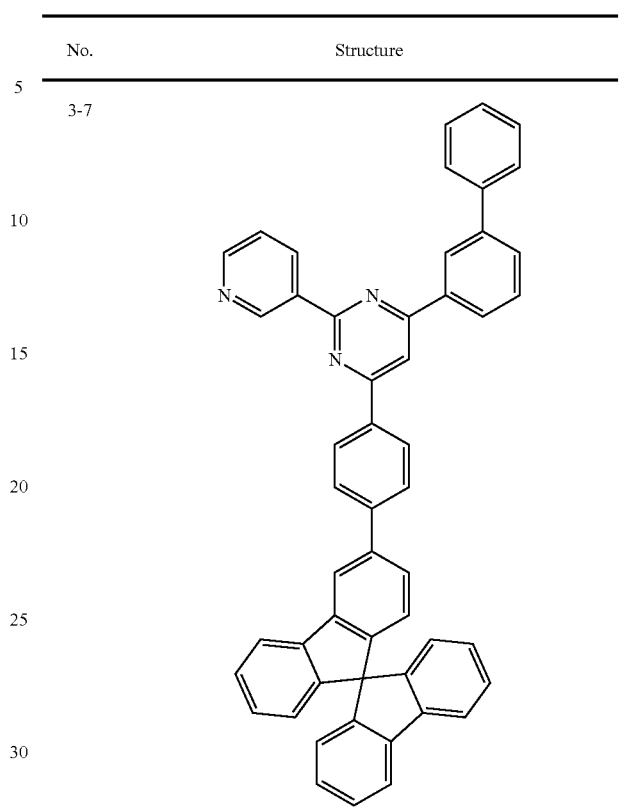

TABLE 1-continued
| No. | Structure |
|---|---|
| 3-9 | 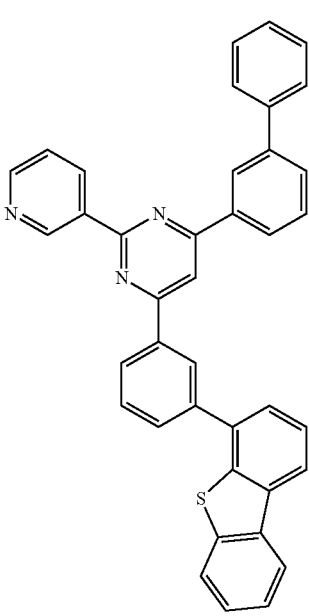 [SMILES: c1ccc(-c2cccc(-c3cc(-c4cccc(-c5cccc6c5sc5ccccc56)c4)nc(-c4cccnc4)n3)c2)cc1] |
| 3-10 | 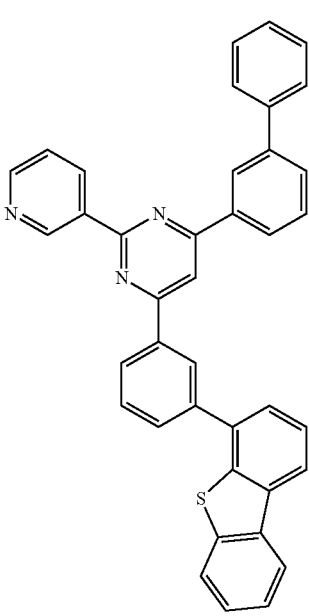 [SMILES: c1ccc(-c2cccc(-c3cc(-c4cccc(-c5cccc6c5sc5ccccc56)c4)nc(-c4cccnc4)n3)c2)cc1] |
| 3-11 | 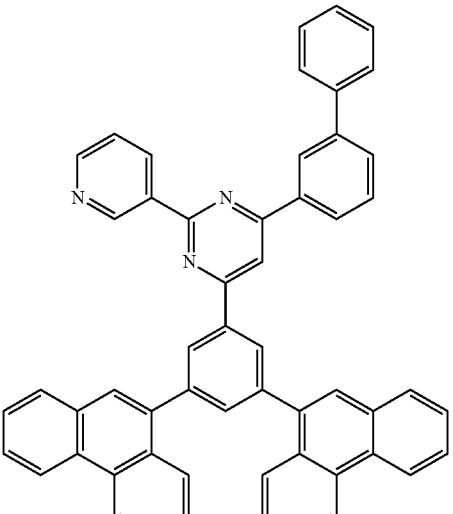 |
| 3-12 | 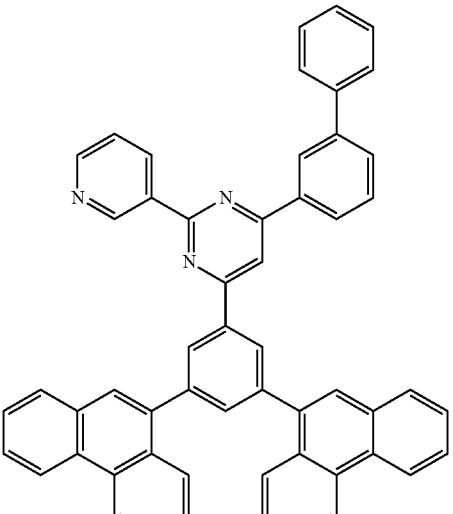 |

TABLE 1-continued
| No. | Structure |
|---|---|
| 3-13 | 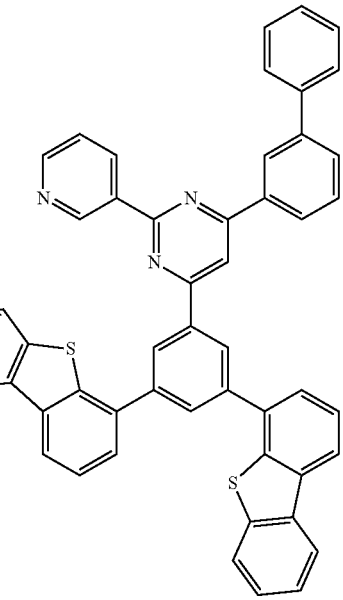 |
| 3-14 | 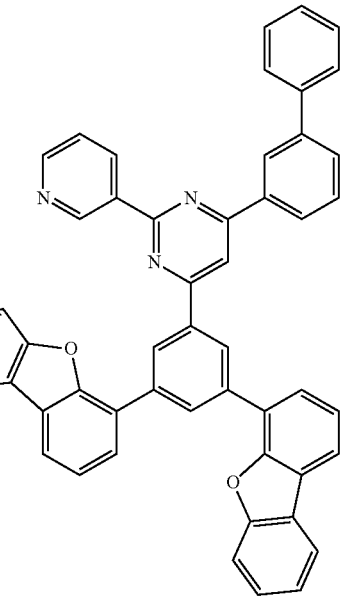 |
An example of the phenyl biphenylpyrimidine compound of formula (I) can be typically synthesized based on the following reaction scheme 1, but the synthesis reaction of the phenyl biphenylpyrimidine compound of formula (I) is not limited thereto.
Reaction Scheme 1
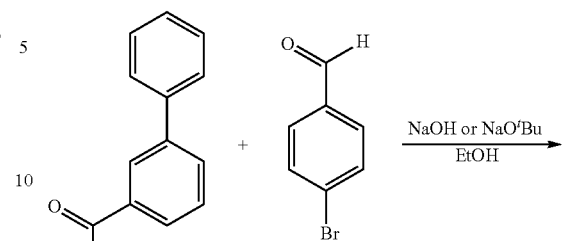
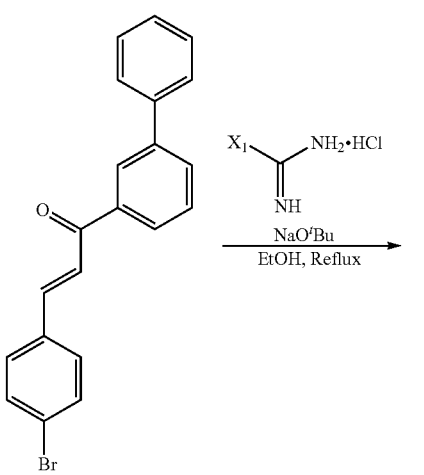
A
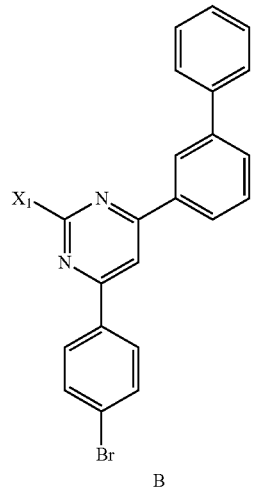
B -continued

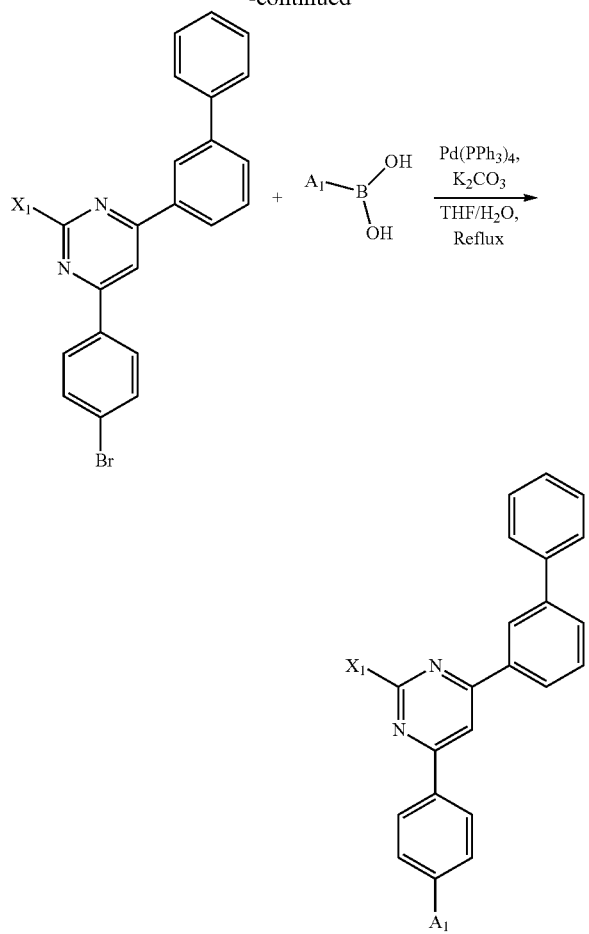

4-bromobenzaldehyde, 3-biphenylethyl ketone and ethanol are respectively added to a reaction flask, and then sodium tert-butoxide (Sodium tert-Butoxide, NaO'Bu) or sodium hydroxide is added to the reaction flask, and the mixture is stir together. The reaction underwent overnight at room temperature. After the reaction is completed, the deionized water is added, and the mixture is stirred and filtered. Filtered solid is first washed with deionized water and methanol, and then the mixture is stirred and filtered with deionized water and methanol. The above washing and filtering steps are repeated twice. After drying, white intermediate A is obtained.

Intermediate A is mixed with different formamidine hydrochloride derivatives and ethanol into a reaction flask, and then the mixture is stirred with sodium t-butoxide or sodium hydroxide in a reaction flask. The mixture is heated and stirred, and maintained at 80° C. for reflux. After the reaction is completed, the reaction is cooled to 60° C. Deionized water is added and the mixture is stirred. An aqueous layer is removed, and the organic layer is concentrated until solids are precipitated. After being washed with ethyl acetate, filtered and dried again, white intermediate B is obtained.

The intermediate B and different boronic acid derivatives and potassium carbonate are placed in a reaction flask, and tetrahydrofuran and deionized water are added. The reaction flask is placed in an oil bath. After being connected with nitrogen and a condenser, heating and stirred is initiated to 80° C. At the same time, tetrakis(triphenylphosphine)palladium (Pd(PPh$_3$)$_4$) is added to the reaction flask to carry out reflux. When the reaction is complete and solids are precipitated, the oil bath is removed. The mixture is filtered after cooling down, and the filtered cake is further added with deionized water, stirred, and filtered. Again, the filtered cake is added to tetrahydrofuran. After heating and stirring until it is completely dissolved, a column containing silica gel is added for purification by chromatography. By being concentrated, a white solid is obtained. After being washed with ethyl acetate, filtered and dried again, a white solid is then obtained as a product.

The present disclosure further provides the organic electroluminescent device, comprising: a cathode; an anode; and an organic layer, being between the cathode and the anode, and comprising the phenyl biphenylpyrimidine compound of formula (I) of the present disclosure.

The organic electroluminescent device of the present disclosure can be the electron transport layer, the electron injection layer, the light emitting layer, the hole blocking layer or the electron blocking layer. In addition to the organic layer, the organic electroluminescent device can further include at least one layer, which is different from the organic layer, and is selected from the group consisting of the electron transport layer, the electron injection layer, the light emitting layer, the hole blocking layer and the electron blocking layer, wherein the light emitting layer further includes fluorescent or phosphorescent dopants, and host materials corresponding to fluorescent or phosphorescent dopants, respectively.

In an embodiment, the organic layer comprising the phenyl biphenylpyrimidine compound of formula (I) is preferably the electron transport layer with a thickness of 20-30 nm; wherein the phenyl biphenylpyrimidine compound of formula (I) can be used as a single material for the electron transport layer, or the phenyl biphenylpyrimidine compound of formula (I) can be used in combination with electrically conductive dopant for the electron transport layer.

In another embodiment, the electron transport layer further comprises an N-type electrically conductive dopant, wherein the N-type electrically conductive dopant and the phenyl biphenylpyrimidine compound of formula (I) of the present disclosure cause chelation, such that the electrons can be more easily injected into the electron transport layer from the cathode, which solves the problem of phase separation and formation of a quenching center caused by poor compatibility of metal and electron transport host materials in the prior art, effectively improving the electron transport efficiency of the electron transport layer.

The N-type electrically conductive dopant system applied to the electron transport layer may be an alkali metal/alkaline earth metal nitrate, carbonate, phosphate or quinolinate. Specifically, examples include lithium carbonate, lithium quinolate (Liq), lithium azide, rubidium carbonate, silver nitrate, barium nitrate, magnesium nitrate, zinc nitrate, cesium nitrate, cesium carbonate, cesium fluoride, and cesium azide. The N-type electrically conductive dopant is preferably lithium quinolate.

In an embodiment, based on the weight of the electron transport layer, the N-type electrically conductive dopant is in an amount of more than 0% by weight up to 50% by weight.

In an embodiment, the organic layer of comprising the phenyl biphenylpyrimidine compound of formula (I) is a stack of the electron transport layer and the hole blocking layer, wherein a thickness of the hole blocking layer is more than 0 nm up to 5 nm.

In another embodiment, for the hole transport layer of the stacked organic layer, the phenyl biphenylpyrimidine compound of formula (I) is used as a single material, and for the electron transport layer of the stacked organic layer, the phenyl biphenylpyrimidine compound of formula (I) is combined with N-type electrically conductive dopant.

The structure of the organic electroluminescent device of the present disclosure will be described in conjunction with the drawings.

FIG. 1 is a schematic cross-sectional view showing an embodiment of the organic electroluminescent device of the present disclosure. The organic electroluminescent device 100 includes substrate 110, the anode 120, the hole injection layer 130, the hole transport layer 140, the light emitting layer 150, the electron transport layer 160, the electron injection layer 170 and the cathode 180. The organic electroluminescent device 100 can be produced by sequentially depositing the above layers.

Figure 2:
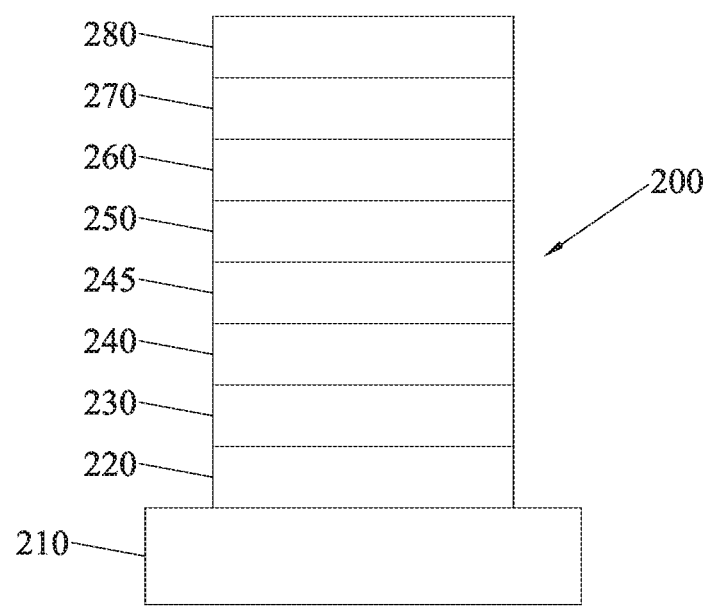
FIG. 2 is a schematic cross-sectional view showing another embodiment of the organic electroluminescent device of the present disclosure.

FIG. 2 is a schematic cross-sectional view showing another embodiment of the organic electroluminescent device of the present disclosure. The organic electroluminescent device 200 includes the substrate 210, the anode 220, the hole injection layer 230, the hole transport layer 240, the electron blocking layer 245, the light emitting layer 250, the electron transport layer 260, the electron injection layer 270 and the cathode 280. Different from FIG. 1, the electron blocking layer 245 is disposed between the hole transport layer 240 and the light emitting layer 250.

Figure 3:
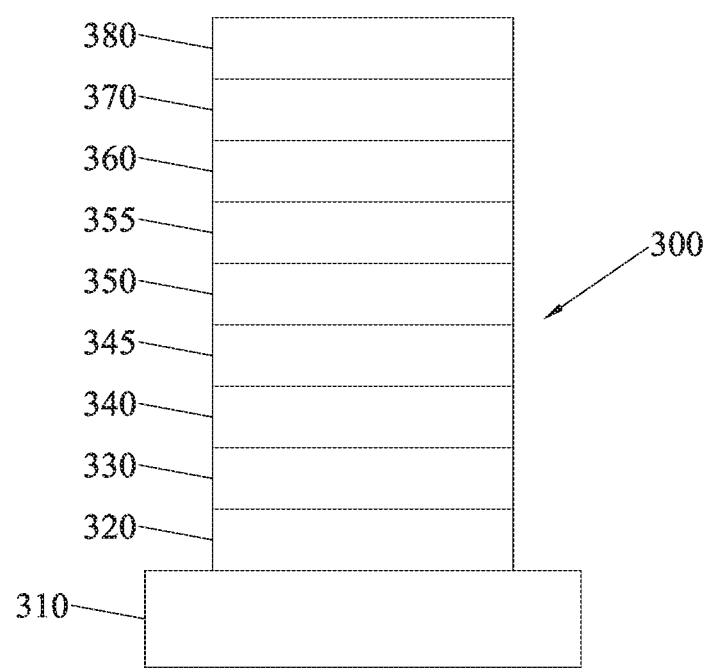
FIG. 3 is a schematic cross-sectional view showing yet another embodiment of the organic electroluminescent device of the present disclosure.

FIG. 3 is a schematic cross-sectional view showing still another embodiment of the organic electroluminescent device of the present disclosure. The organic electroluminescent device 300 includes the substrate 310, the anode 320, the hole injection layer 330, the hole transport layer 340, the electron blocking layer 345, the light emitting layer 350, the hole blocking layer 355, the electron transport layer 360, the electron injection layer 370 and the cathode 380. Different from FIG. 2, the hole blocking layer 355 is disposed between the light emitting layer and the electron transport layer 360.

The organic electroluminescent device can be produced based on inverted structures of the components shown in FIGS. 1 to 3. One or more layers are added or removed as needed for such inverted structures.

Materials of the hole injection layer, the hole transport layer, the electron blocking layer, the hole blocking layer, the electron blocking layer, the electron injection layer can be conventionally selected materials. For example, the electron transporting material forming the electron transport layer is different from the material of the light emitting layer, and has a hole transporting property, thereby facilitating migration of the hole in the electron transport layer and preventing the accumulation of carriers caused by the dissociation energy difference of the light emitting layer and the electron transport layer.

Due to that the phenyl biphenylpyrimidine compound of formula (I) of the present disclosure, used for the electron transport layer or the hole blocking layer, has a triplet state energy ($E_T$) of higher than 2.4 eV and an extremely low maximum occupied molecular orbital (HOMO) energy level and good carrier mobility, the hole in the light emitting layer is not easily lost; and at the same time, the electrons are efficiently transmitted to the light emitting layer, which helps the density of the electrons and holes in the light emitting layer to be balanced. The luminous efficiency and drive stability are increased.

Further, U.S. Pat. No. 5,844,363 discloses a flexible and transparent substrate in combination with an anode, which is incorporated herein by reference in its entirety. As disclosed in US Patent Publication No. 20030230980A1, an example of a p-type doped hole transport layer is m-MTDATA doped with $F_4$-TCNQ at a molar ratio of 50:1, which is incorporated herein by reference in its entirety. As disclosed in US Patent Publication No. 20030230980A1, an example of an n-type doped electron transport layer is BPhen doped with Li at a molar ratio of 1:1, which is incorporated herein by reference in its entirety. Entire disclosures of an exemplary cathode of U.S. Pat. Nos. 5,703,436 and 5,707,745 are incorporated herein by reference in their entirety, wherein the cathodes each has a thin layer of metal, e.g., Mg/Ag (Mg:Ag), with an overlaying transparent, electrically conductive and sputter-deposited ITO layer. Theory and use of each of blocking layers are described in U.S. Pat. No. 6,097,147 and US Patent Publication No. 20030230980, which are incorporated herein by reference in their entirety. An injection layer, and a protective layer are described in US Patent Publication No. 20040174116A1, which is incorporated herein by reference in its entirety.

Structures and materials which are not specifically described may also be applied to the present disclosure, for example, an organic electroluminescent device comprising polymeric materials (PLEDs) disclosed in U.S. Pat. No. 5,247,190, which is incorporated herein by reference in its entirety. Furthermore, an organic electroluminescent device formed by stacking disclosed in U.S. Pat. No. 5,707,745 may be used, which is incorporated herein by reference.

Unless otherwise specified, any layers in the different examples may be deposited by any suitable method. For an organic layer, preferred methods include, for example, thermal evaporation and jet printing described in U.S. Pat. Nos. 6,013,982 and 6,087,196, which are incorporated herein by reference in their entirety; organic vapor phase deposition (OVPD) disclosed in U.S. Pat. No. 6,337,102, which is incorporated herein by reference in its entirety; and deposition by organic vapor jet printing (OVJP) disclosed in U.S. patent application Ser. No. 10/233,470, which is incorporated by reference in its entirety. Other suitable deposition methods include spin-coating and other solution-based processes. It is preferable to conduct solution-based processes in an environment containing nitrogen or inert gas. For other layers, preferred methods include thermal evaporation. Preferred patterning methods include, for example, deposition through a mask followed by cold welding, and patterning and deposition by integrated ink-jet and OVJD, as described in U.S. Pat. Nos. 6,294,398 and 6,468,819, which are incorporated by reference in their entirety. Certainly, other methods may be used. Materials to be deposited may be modified to be compatible with particular deposition methods.

The phenyl biphenylpyrimidine compound of formula (I) of the present disclosure may be used to make amorphous thin layers applied to an organic electroluminescent device by vacuum deposition or spin-coating. When the compound is used in any of the organic layers described above, it exhibits a longer lifetime and better thermal stability with high efficiency and a low driving voltage.

The organic electroluminescent device of the present disclosure is applicable to a single device, which is one having a structure of an array or a cathode and an anode arranged in an X-Y coordinates of the array. Compared to conventional components, the present disclosure can significantly increase the lifetime of the organic electroluminescent device.

The various properties and effects of the present disclosure are described in detail below by way of examples. The detailed description is only illustrative of the nature of the disclosure, and the disclosure is not limited to the specific embodiments.

Synthesis Example 1: Synthesis of Compound 2-1

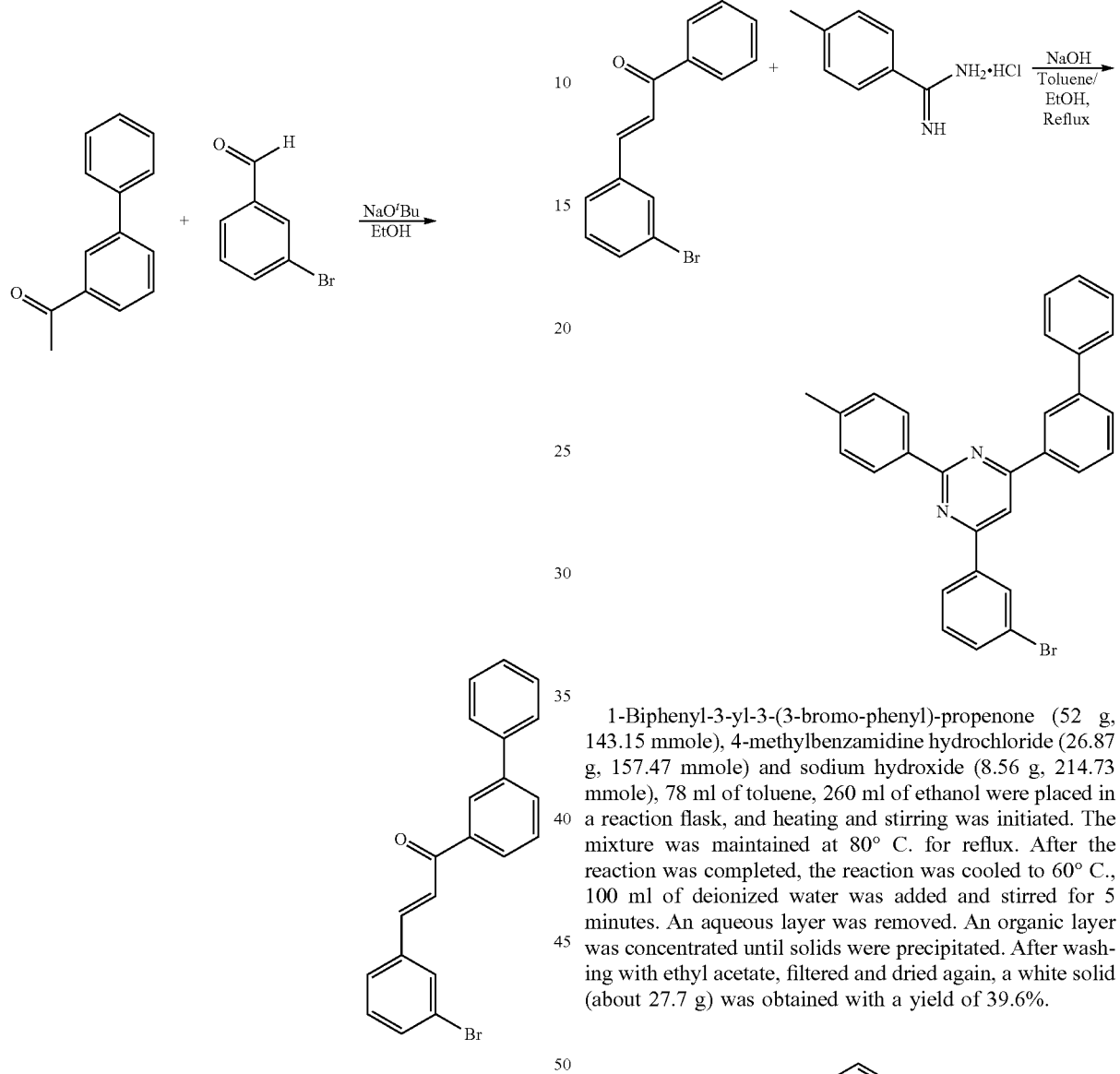

3-Acetylbiphenyl (30 g, 164.6 mmole), 3-bromobenzaldehyde (29.01 g, 156.79 mmole) and 600 ml of ethanol were added and stirred in a reaction flask. Then, sodium tert-butoxide (22.58 g, 235.19 mmole) was added, and the mixture was stirred at room temperature. After the reaction was completed, 200 ml of deionized water was added, the mixture was stirred and filtered. The filtered solid was first washed with deionized water and methanol, and then stirred with 100 ml of deionized water and 200 ml of methanol for 30 minutes. After filtration and repeating the above washing and filtering step twice, the solid was dried to obtain a white solid (about 52 g), which was 1-Biphenyl-3-yl-3-(3-bromo-phenyl)-propenone), with a yield of 92.3%.

1-Biphenyl-3-yl-3-(3-bromo-phenyl)-propenone (52 g, 143.15 mmole), 4-methylbenzamidine hydrochloride (26.87 g, 157.47 mmole) and sodium hydroxide (8.56 g, 214.73 mmole), 78 ml of toluene, 260 ml of ethanol were placed in a reaction flask, and heating and stirring was initiated. The mixture was maintained at 80° C. for reflux. After the reaction was completed, the reaction was cooled to 60° C., 100 ml of deionized water was added and stirred for 5 minutes. An aqueous layer was removed. An organic layer was concentrated until solids were precipitated. After washing with ethyl acetate, filtered and dried again, a white solid (about 27.7 g) was obtained with a yield of 39.6%.

-continued

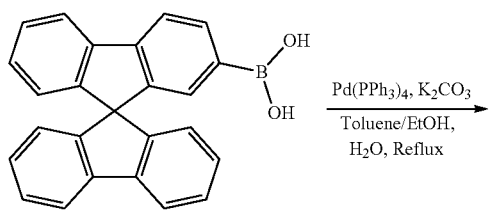

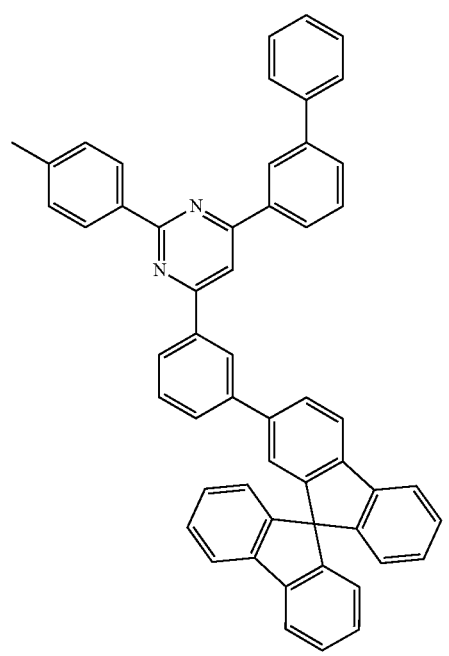

Synthesis Example 2: Synthesis of Compound 2-2

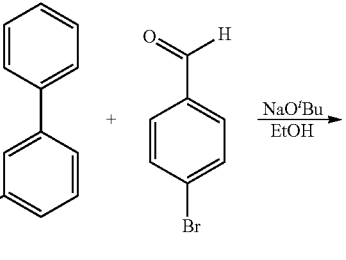

4-Biphenyl-3-yl-6-(3-bromo-phenyl)-2-p-tolyl-pyrimidine) (4.32 g, 12 mmole), Spiro-9,9'-bifluorene-2-borylic acid (4.78 g, 10 mmole) and potassium carbonate (6.73 g, 35 mmole) were added in a reaction flask. Then, 34 ml of toluene, 10 ml of ethanol, 14 ml of deionized water were added thereto. The reaction flask was placed in an oil bath. After connecting to nitrogen and a condenser, heating and stirring was initiated to 80° C. Tetrakis(triphenylphosphine) palladium (Pd(PPh₃)₄) (0.58 g, 0.5 mmole) was added in the reaction flask. When the reaction was complete and solids were precipitated, the oil bath was removed, and the mixture was cooled before being filtered. The filtered cake was further added with 100 ml of deionized water, stirred for 10 minutes, and filtered again. The filter cake was added to 250 ml of tetrahydrofuran, and the mixture was heated and stirred until it was completely dissolved. Then, the mixture was added to a column packed with 20 g of silica gel, and purified by chromatography, and concentrated to a white solid, which was then washed with ethyl acetate, filtered and dried. A white solid (about 6.1 g) was obtained as a product with a yield of 85.5%.

$^1$H NMR (CDCl$_3$, 400 MHz), δ8.56 (d, 2H), 8.44 (t, 1H), 8.36 (t, 1H), 8.22 (t, 1H), 8.14 (t, 1H), 7.98 (d, 2H), 7.90 (d, 1H), 7.86 (d, 2H), 7.73-7.77 (m, 2H), 7.69-7.72 (m, 2H), 7.63 (t, 1H), 7.56 (t, 1H), 7.47-7.53 (m, 3H), 7.32-7.45 (m, 6H), 7.11-7.15 (m, 3H), 7.04 (t, 1H), 6.81 (d, 2H), 6.76 (d, 1H), 2.47 (s, 3H).

3-Acetylbiphenyl (19.6 g, 100 mmole) and 4-bromobenzaldehyde (18.5 g, 100 mmole) were added in a 500 ml two-neck round bottom reaction flask. After adding 200 ml of ethanol and potassium hydroxide (2.8 g, 50 mmole) respectively, the mixture was stirred at room temperature. After the reaction was completed, the solid was filtered, washed with ethanol and dried to give a pale-yellow solid (about 31.3 g) with a yield of 86%.

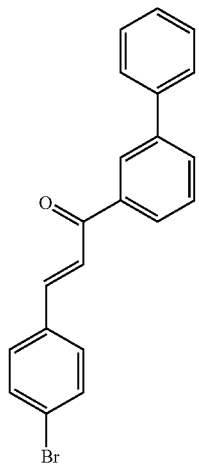

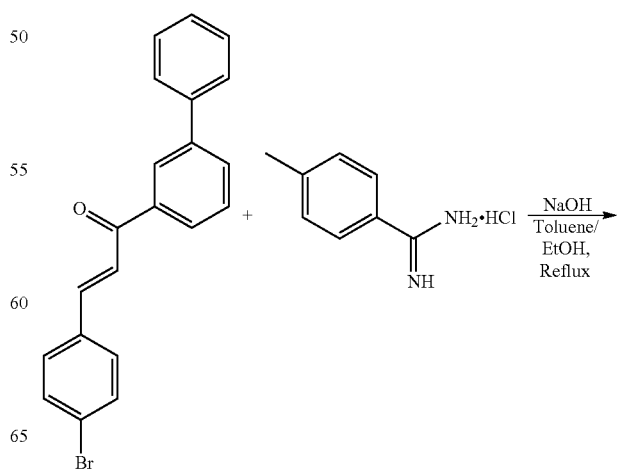

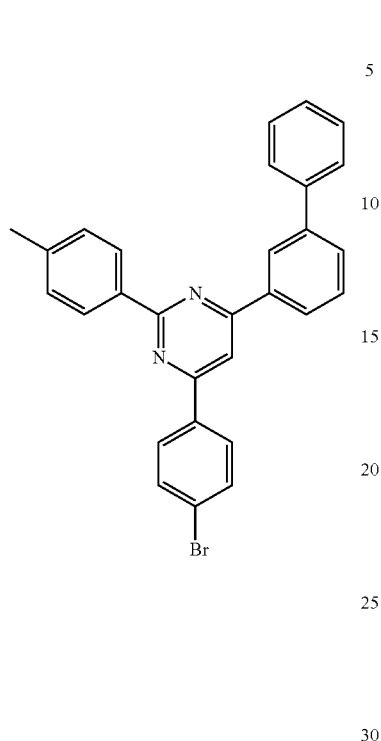

1-Biphenyl-3-yl-3-(4-bromo-phenyl)-propenone (51 g, 140.4 mmole), 4-methylbenzamidine hydrochloride (26.35 g, 154.44 mmole) with sodium hydroxide (8.42 g, 210.6 mmole), 77 ml of toluene, and 255 ml of ethanol were added in a reaction flask; heating and stirring was initiated, and the mixture was maintained at 80° C. for reflux. After the reaction was completed, the reaction was cooled to 60° C. 100 ml of deionized water was added. After stirring for 5 minutes, the aqueous layer was removed, the organic layer was concentrated until solids were precipitated. After being washed with ethyl acetate, filtered and dried, a white solid (about 27 g) was obtained in a yield of 40.28%.

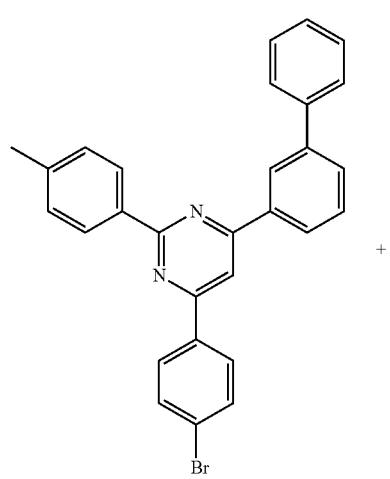

+

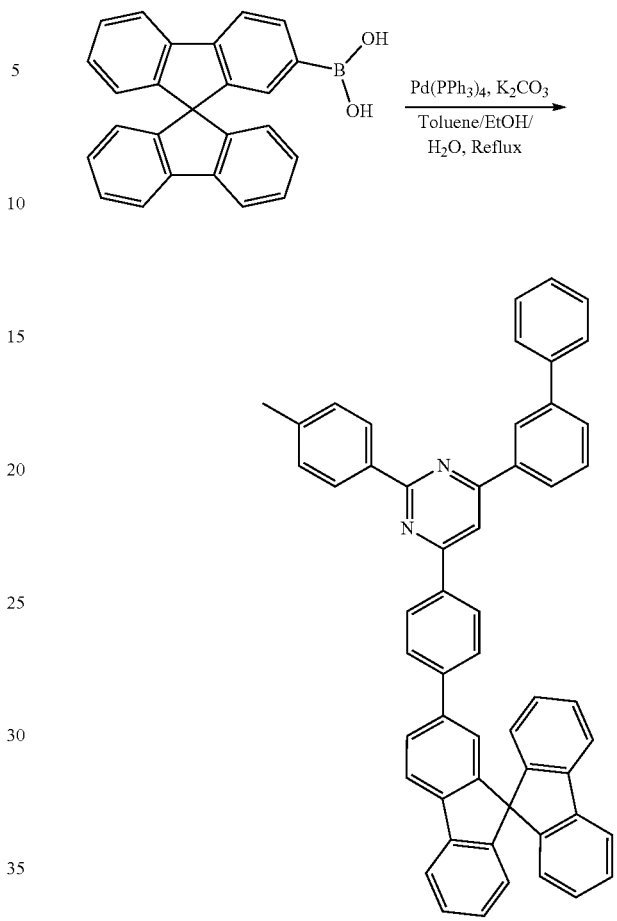

4-Biphenyl-3-yl-6-(4-bromo-phenyl)-2-p-tolyl-pyrimidine (4.32 g, 12 mmole), Spiro-9,9'-bifluorene-2-boronic acid (4.78 g, 10 mmole) and potassium carbonate (6.73 g, 35 mmole) was placed in a reaction flask. Then, 34 ml of toluene, 10 ml of ethanol, 14 ml of deionized water were added therein, and the reaction flask was placed in an oil bath. After connecting to nitrogen and condenser, heating and stirring was initiated to 80° C. Tetrakis(triphenylphosphine)palladium (Pd(PPh$_3$)$_4$) (0.58 g, 0.5 mmole) was added to the reaction flask. When the reaction was complete and solids were precipitated, the oil bath was removed. The mixture was cooled before being filtered. The filtered cake was further added with 100 ml of deionized water. After stirring for 10 minutes, it was filtered again, and the filtered cake was added to 250 ml of tetrahydrofuran, and the mixture was heated and stirred until it was completely dissolved. Then, the mixture was added to a column packed with 20 g of silica gel, purified by chromatography, and concentrated to a white solid. After washing with ethyl acetate, filtered again and dried, a white solid (about 6.3 g) was obtained with a yield of 88.3%.

$^1$H NMR (CDCl$_3$, 400 MHz), δ8.60 (d, 2H), 8.45 (t, 1H), 8.25 (d, 2H), 8.22 (d, 1H), 7.98 (s, 1H), 7.95 (d, 1H), 7.88 (t, 3H), 7.69-7.76 (m, 4H), 7.60-7.64 (m, 3H), 7.50 (t, 2H), 7.38-7.43 (m, 4H), 7.33 (d, 2H), 7.13 (t, 3H), 7.03 (s, 1H), 6.81 (d, 2H), 6.75 (d, 1H), 2.45 (s, 3H).

Synthesis Example 3: Synthesis of Compound 2-4

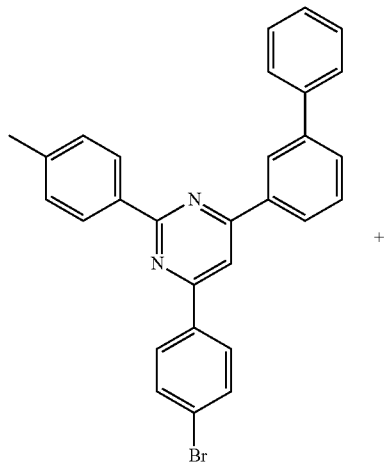

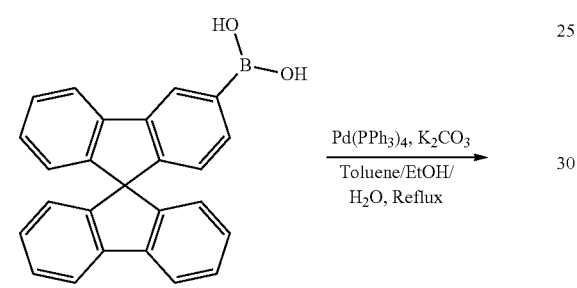

4-Biphenyl-3-yl-6-(4-bromo-phenyl)-2-p-tolyl-pyrimidine (4.32 g, 12 mmole) with Spiro-9,9'-bifluorene-2-boronic acid (4.78 g, 10 mmole) and potassium carbonate (6.73) g, 35 mmole) was placed in a reaction flask. 34 ml of toluene, 10 ml of ethanol, 14 ml of deionized water were then added therein, and the reaction flask was placed in an oil bath, connecting to nitrogen and a condenser. Then, heating and stirring was initiated to 80° C. At the same time, tetrakis(triphenylphosphine)palladium (Pd(PPh$_3$)$_4$) (0.58 g, 0.5 mmole) was added to the reaction flask. When the reaction was completed and solids were precipitated, the oil bath was removed, and the mixture was cooled before being filtered. The filtered cake was further added with 100 ml of deionized water. After stirring for 10 minutes, it was filtered again. The filter cake was added to 250 ml of tetrahydrofuran, and the mixture was heated and stirred until it was completely dissolved. Then, the mixture was added to a column packed with 20 g of silica gel, purified by chromatography, and concentrated to a white solid. After washing with ethyl acetate, filtered again and dried, a white solid (about 5.9 g) was obtained with a yield of 82.69%.

$^1$H NMR (CDCl$_3$, 400 MHz), δ8.64 (d, 2H), 8.50 (t, 1H), 8.42 (d, 2H), 8.18 (t, 1H), 8.14 (d, 1H), 8.09 (s, 1H), 7.95 (d, 1H), 7.85-7.89 (m, 4H), 7.78 (t, 1H), 7.72-7.74 (m, 2H), 7.65 (t, 1H), 7.53 (t, 2H), 7.35-7.44 (m, 7H), 7.13-7.17 (m, 3H), 6.85 (d, 1H), 6.77-6.82 (m, 3H), 2.47 (s, 3H).

Synthesis Example 4: Synthesis of Compound 3-4

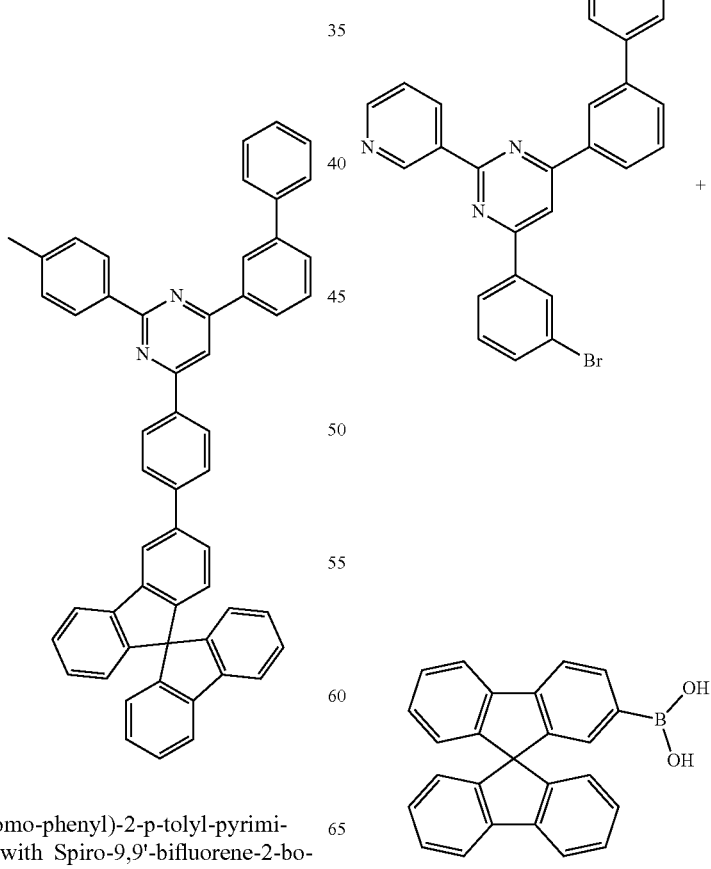

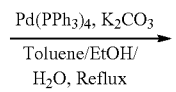

Synthesis Example 5: Synthesis of Compound 3-6

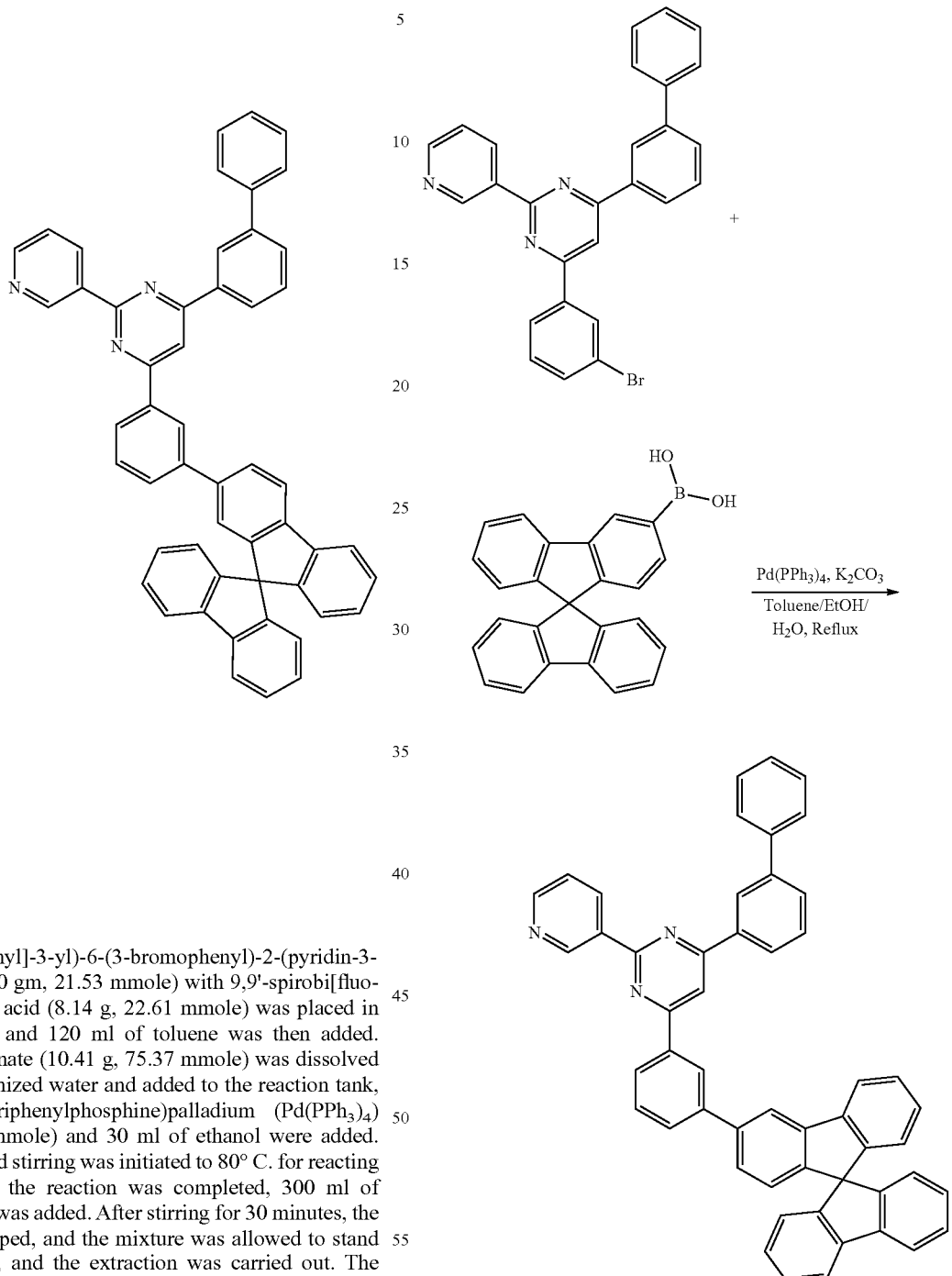

4-([1,1'-biphenyl]-3-yl)-6-(3-bromophenyl)-2-(pyridin-3-yl)pyrimidine (10 gm, 21.53 mmole) with 9,9'-spirobi[fluoren]-2-ylboronic acid (8.14 g, 22.61 mmole) was placed in a reaction tank, and 120 ml of toluene was then added. Potassium carbonate (10.41 g, 75.37 mmole) was dissolved in 70 ml of deionized water and added to the reaction tank, while tetrakis(triphenylphosphine)palladium (Pd(PPh$_3$)$_4$) (1.24 g, 1.077 mmole) and 30 ml of ethanol were added. Then, heating and stirring was initiated to 80° C. for reacting overnight. After the reaction was completed, 300 ml of deionized water was added. After stirring for 30 minutes, the stirring was stopped, and the mixture was allowed to stand for stratification, and the extraction was carried out. The extracted filtrate was added to a column packed with silica gel, and purified by chromatography. After concentrating to the thick state, 300 ml of hexane was added to strengthen the precipitation, and an organic layer was combined to filter the solid to obtain a milky white solid (about 7 g).

$^1$H NMR (CDCl$_3$, 400 MHz), δ9.90 (d, 1H), 8.96 (td, 1H), 8.76 (dd, 1H), 8.47 (s, 1H), 8.35 (s, 1H), 8.21 (d, 1H), 8.14 (d, 1H), 8.03 (s, 1H), 7.99 (d, 1H), 7.91 (d, 1H), 7.86 (d, 2H), 7.74-7.79 (m, 2H), 7.71 (d, 2H), 7.64 (t, 1H), 7.58 (d, 1H), 7.36-7.54 (m, 8H), 7.12-7.16 (m, 3H), 7.04 (d, 1H), 6.82 (d, 2H), 6.77 (d, 1H).

4-([1,1'-biphenyl]-3-yl)-6-(3-bromophenyl)-2-(pyridin-3-yl)pyrimidine (10 g, 21.53 mmole) with spiro-9,9'-bifluorene-2-boronic acid (9.41 g, 22.61 mmole) was placed in a reaction tank and 120 ml of toluene was added. Potassium carbonate (10.41 g, 75.37 mmole) was dissolved in 70 ml of deionized water and added to the reaction tank, while tetrakis(triphenylphosphine)palladium (Pd(PPh$_3$)$_4$) (1.24 g, 1.077 mmole) and 30 ml of ethanol were added. Then, heating and stirring was initiated to 80° C. for reacting overnight. After the reaction was completed, 300 ml of deionized water was added. After stirring for 30 minutes, the stirring was stopped, and the mixture was allowed to stand for stratification, and the extraction was carried out. The extracted filtrate was added to a column packed with silica gel, and purified by chromatography. After concentrating to the thick state, 300 ml of hexane was added to enhance the precipitation, and an organic layer was combined to filter the solid to give a milky white solid (about 6 g).

$^1$H NMR (CDCl$_3$, 400 MHz), δ9.97 (d, 1H), 8.97 (td, 1H), 8.77 (dd, 1H), 8.55 (s, 1H), 8.52 (t, 1H), 8.24-8.29 (m, 2H), 8.15 (s, 2H), 7.97 (d, 1H), 7.90 (d, 2H), 7.84 (d, 1H), 7.79 (d, 1H), 7.72 (d, 2H), 7.64-7.69 (m, 2H), 7.52 (t, 2H), 7.40-7.48 (m, 5H), 7.17 (t, 3H), 6.88 (d, 1H), 6.84 (d, 2H), 6.80 (d, 1H).

Synthesis Example 6: Synthesis of Compound 3-7

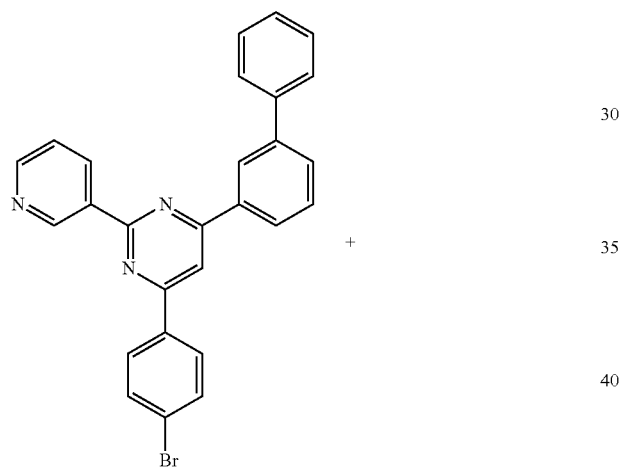

+

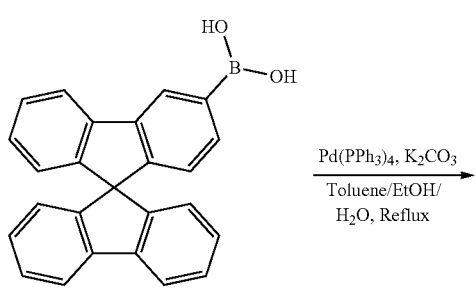

Pd(PPh$_3$)$_4$, K$_2$CO$_3$
Toluene/EtOH/
H$_2$O, Reflux

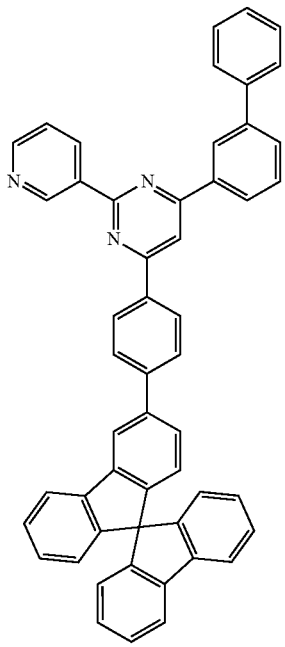

4-[1,1'-biphenyl]-3-yl-6-(4-bromophenyl)-2-(pyridine-3-yl)pyrimidine) (9.28 g, 20 mmole) with 9,9'-spirobifluorene-3-ylborylic acid (9.3 g, 24 mmole) and tetrakis(triphenylphosphine) palladium (Pd(PPh$_3$)$_4$) (1.16 g, 1 mmole) and potassium carbonate (5.5 g, 40 mmole) was placed in a 1000 ml double neck round bottom reaction flask. 320 ml of toluene, 220 ml of ethanol and 100 ml of deionized water were added therein respectively. The reaction flask was placed in an oil bath, connecting to nitrogen and a condenser. Then, heating and stirring was initiated to 80° C. When the reaction was completed and solids were precipitated, the oil bath was removed, and the mixture was cooled before being filtered. The filtered solid was washed again with 300 ml of acetone and dried to give a white solid (about 8.9 g) in a yield of 64%.

$^1$H NMR (CDCl3, 400 MHz) δ9.96 (s, 1H), 8.99 (td, 1H), 8.77 (dd, 1H), 8.52 (t, 1H), 8.42 (d, 2H), 8.27 (d, 1H), 8.17 (s, 1H), 8.14 (d, 1H), 7.96 (d, 1H), 7.88 (d, 4H), 7.80 (d, 1H), 7.73 (dd, 2H), 7.67 (t, 1H), 7.53 (t, 2H), 7.45-7.51 (m, 1H), 7.38-7.44 (m, 5H), 7.13-7.16 (m, 3H), 6.86 (s, 1H), 6.81 (d, 2H), 6.78 (d, 1H).

Synthesis Example 7: Synthesis of Compound 3-8

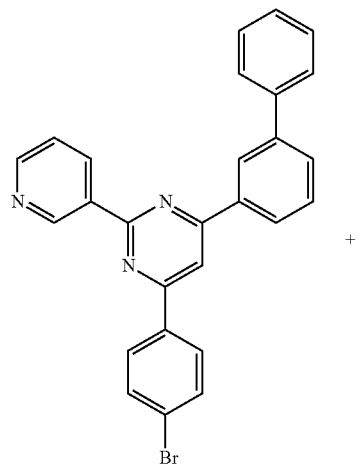

+

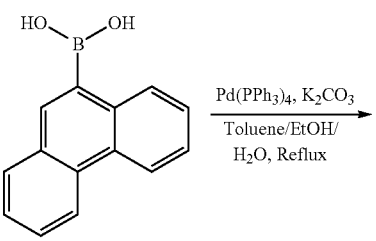

Pd(PPh$_3$)$_4$, K$_2$CO$_3$
Toluene/EtOH/
H$_2$O, Reflux
→

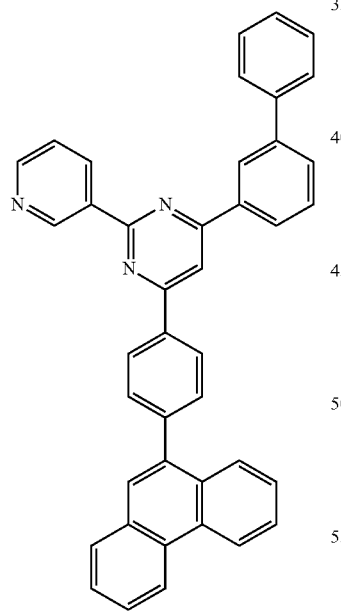

4-([1,1'-biphenyl]-3-yl)-6-(4-bromophenyl)-2-(pyridin-3-yl)pyrimidine (9.28 g, 20 mmole), phenanthrene-9-yl-9-boronic acid (5.3 g, 24 mmole), tetrakis(triphenylphosphine) palladium (Pd(PPh$_3$)$_4$) (1.16 g, 1 mmole) and potassium carbonate (5.5 g, 40 mmole) were placed in a 1000 ml two-neck round bottom reaction flask. 320 ml of Toluene, 220 ml of ethanol and 100 ml of deionized water were placed therein respectively, and the reaction flask was placed in an oil bath. After connecting to nitrogen and a condenser, heating and stirring was initiated to 80° C. When the reaction was completed and solids were precipitated, the oil bath was removed. It was cooled before being filtered. After drying, a gray-black solid (about 5.4 g) was obtained in a yield of 48%.

$^1$H NMR (CDCl$_3$, 400 MHz) δ9.98 (d, 1H), 9.01 (td, 1H), 8.82 (d, 1H), 8.78 (d, 1H), 8.76 (d, 1H), 8.55 (s, 1H), 8.46 (d, 2H), 8.30 (dd, 1H), 8.23 (s, 1H), 7.90 (d, 1H), 7.95 (d, 1H), 7.77-7.82 (m, 3H), 7.65-7.64 (m, 3H), 7.66-7.78 (m, 7H), 7.58 (t, 1H), 7.52 (t, 2H), 7.50 (d, 1H), 7.49 (d, 1H), 7.44 (t, 1H).

Synthesis Example 8: Synthesis of Compound 1-2

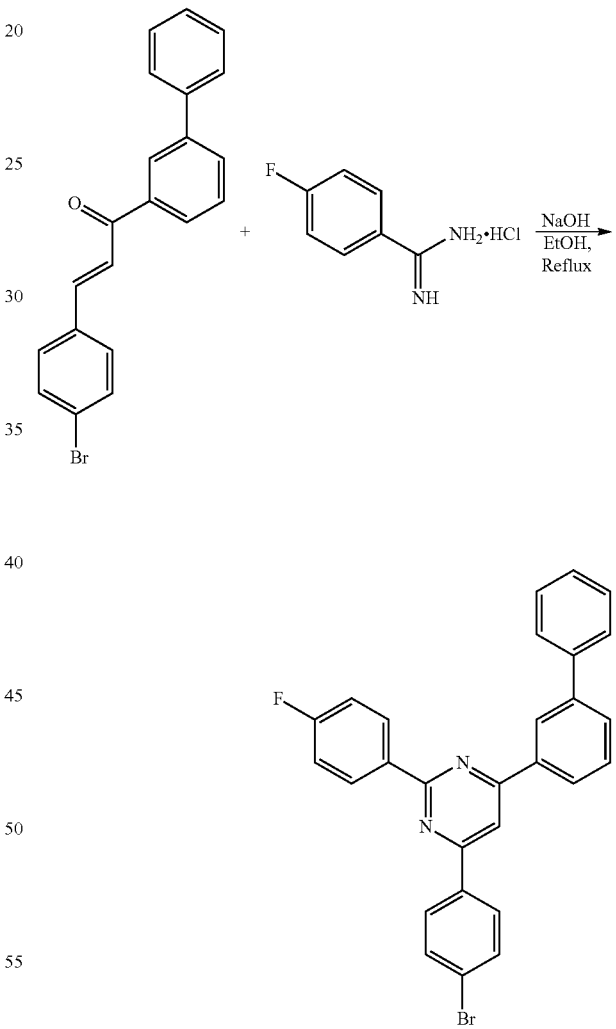

1-biphenyl-3-yl-3-(4-bromo-phenyl)-propenone (36.7 g, 101.14 mmole), 4-fluorobenzamidine hydrochloride (17.66 g, 101.14 mmole) and sodium hydroxide (5.78 g, 144.5 mmole) and 200 ml of ethanol were placed in the reaction flask. Then, heating was initiated to 75° C. for reacting overnight. After completion of the reaction, filtration was carried out to obtain a milky white solid (about 23 g).

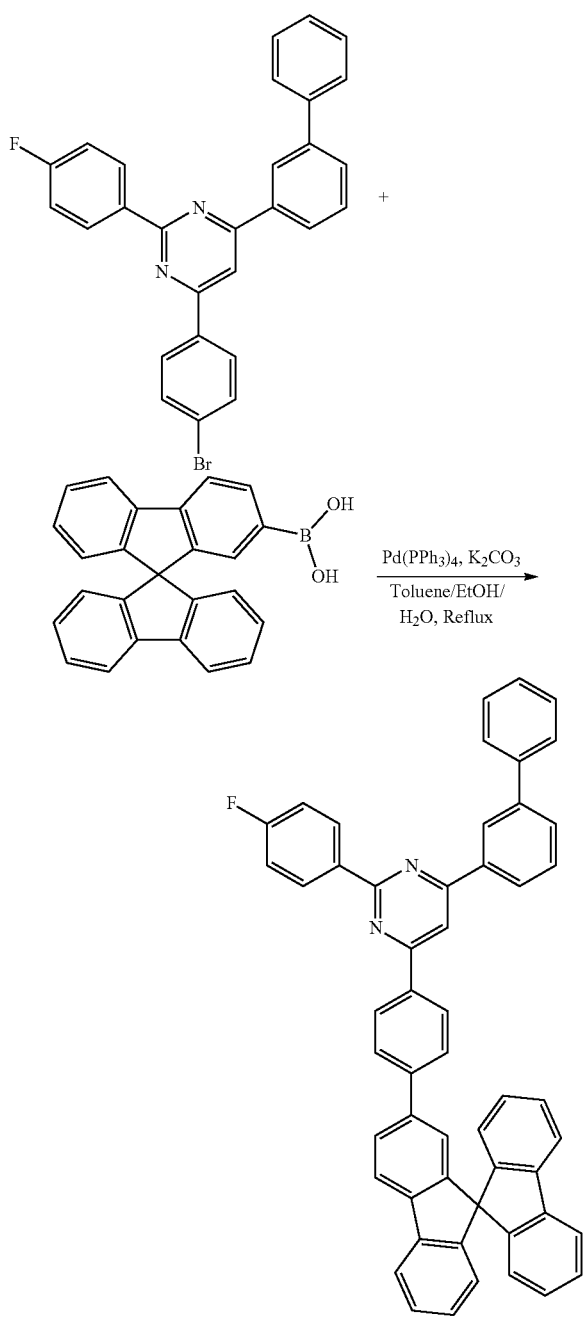

4-([1,1'-biphenyl]-3-yl)-6-(4-bromophenyl)-2-(4-fluorophenyl)pyrimidine (10 g, 20.77 mmole) with 9,9'-spirobi[fluoren]-2-ylboronic acid (7.85 g, 21.8 mmole) was placed in a reaction tank, and 120 ml of toluene was added. Potassium carbonate (10 g, 72.7 mmole) was dissolved in 70 ml of deionized water and added to the reaction tank, while tetrakis(triphenylphosphine)palladium (Pd(PPh$_3$)$_4$) (1.2 g, 1.039 mmole) and 30 ml of ethanol were added. Then, heating was initiated to 80° C. for reacting overnight. After the reaction was completed, 300 ml of deionized water was added. After stirring for 30 minutes, the stirring was stopped, and the mixture was allowed to stand for stratification, extraction was carried out, and the column packed with silica gel was added for chromatographic purification. After concentrating to a thick state, 300 ml of hexane was added to strengthen the precipitation, and the solid was filtered to give a milky white solid (about 6 g).

$^1$H NMR (CDCl$_3$, 400 MHz) δ8.69-8.72 (m, 2H), 8.44 (t, 1H), 8.23 (d, 2H), 8.20 (d, 1H), 8.00 (s, 1H), 7.96 (d, 1H), 7.87-7.90 (m, 3H), 7.75 (d, 1H), 7.69-7.73 (m, 3H), 7.61-7.64 (m, 3H), 7.50 (t, 2H), 7.38-7.43 (m, 4H), 7.19 (t, 2H), 7.14 (t, 3H), 7.04 (d, 1H), 6.81 (d, 2H), 6.75 (d, 1H)

The physical property values of the above materials and the compound EET09 are shown in Table 2, wherein the compound EET09 is as described in Japanese Patent No. 2011003793A.

The method of measuring each physical property value is as follows.

The method of measuring each physical property value is as follows.

(1) Thermal Cracking Temperature (T$_d$)

The thermogravimetric analysis was performed using a thermogravimetric analyzer (Perkin Elmer, TGA 8000), and the pyrolysis properties of the obtained compound were measured, under normal pressure and nitrogen atmosphere, at a programmed temperature of 20° C./min. The temperature at which the weight is reduced to 95% of the initial weight is the thermal cracking temperature (T$_d$).

(2) Glass Transition Temperature (T$_g$)

The prepared compound was measured using a differential scanning calorimeter (DSC; Perkin Elmer, DSC 8000) at a programmed temperature rate of 20° C./min.

(3) The Energy Level of the Highest Occupied Molecular Orbital (HOMO)

In addition, the compound was made into a thin film state, and its ionization potential value was measured under the atmosphere using a photoelectron spectrophotometer (Riken Keiki, Surface Analyzer), and the value was further converted to a HOMO energy level value.

(4) the Lowest Unoccupied Molecular Orbital (LUMO) Energy Level Value

The film of the above compound was measured by a UV/VIS spectrophotometer (Perkin Elmer, Lambda 20) to measure the boundary value of the absorption wavelength, and the value was converted into an energy gap value, and the value of the energy gap was added to the value of the HOMO energy level. Then, the LUMO energy level is obtained.

(5) Triplet Energy Value (E$_T$)

The luminescence spectrum was measured using a fluorescence spectrometer (Perkin Elmer, LS 55) at a temperature of 77 K, and E$_T$ was obtained by calculation.

TABLE 2

| Compound type | | T$_d$ (° C.) | T$_g$ (° C.) | HOMO (eV) | LUMO (eV) | E$_T$ (eV) |
|---|---|---|---|---|---|---|
| Comparative example | EET09 | 440 | 123 | 5.75 | 2.74 | 2.85 |
| Synthesis example 1 | 2-1 | 501 | 138 | 6.12 | 2.53 | 2.53 |
| Synthesis example 2 | 2-2 | 515 | 147 | 6.04 | 2.78 | 2.40 |
| Synthesis example 3 | 2-4 | 507 | 145 | 6.09 | 2.71 | 2.52 |
| Synthesis example 4 | 3-4 | 504 | 165 | 6.04 | 2.42 | 2.50 |
| Synthesis example 5 | 3-6 | 508 | 142 | 6.05 | 2.43 | 2.61 |
| Synthesis example 6 | 3-7 | 511 | 147 | 6.04 | 2.63 | 2.52 |
| Synthesis example 7 | 3-8 | 491 | 102 | 6.05 | 2.61 | 2.42 |
| Synthesis example 8 | 1-2 | 506 | 144 | 6.01 | 2.68 | 2.48 |

Preparation Example 1-1: Production of the Organic Electroluminescent Device

Prior to being loaded into an evaporation system, a substrate was cleaned and then degreased with a solvent and UV ozone. The substrate was then transferred into a vacuum deposition chamber for deposition of all layers on top of the substrate. By evaporation on a heated boat under a vacuum of about $10^{-6}$ Torr, each of the layers was deposited in sequence as shown in FIG. 2:

a) a hole injection layer, having a thickness of 20 nm, and comprising HTM doped with a P-type electrically conductive dopant of 6% by weight, wherein the P-type electrically conductive dopant is purchased from Shanghai Yufeng Chemical Co., Ltd., and HTM is purchased from Merck & Co., Inc.;

b) a hole transport layer, having a thickness of 150 nm, HTM;

c) an exciton blocking layer, having a thickness of 10 nm, HT (prepared by e-Ray Optoelectronics Technology);

d) a light emitting layer, having a thickness of 25 nm, comprising EBH doped with 4% by weight of BD, wherein BD and EBH are prepared by e-Ray Optoelectronics Technology;

e) an electron transport layer, having a thickness of 20 nm, and comprising Compound 2-4 and doped lithium quinolate (Liq), the weight ratio is 5:5;

f) an electron injection layer, having a thickness of 1.5 nm, Liq; and g) a cathode, having a thickness of about 180 nm, and comprising aluminum (Al).

The device structure of Preparation example 1-1 may be denoted as ITO/HTM: P-type electrically conductive dopant (20 nm)/HTM (150 nm)/HT (10 nm)/EBH: BD (25 nm)/Compound 2-4: Liq (20 nm)/Liq (1.5 nm)/Al (180 nm).

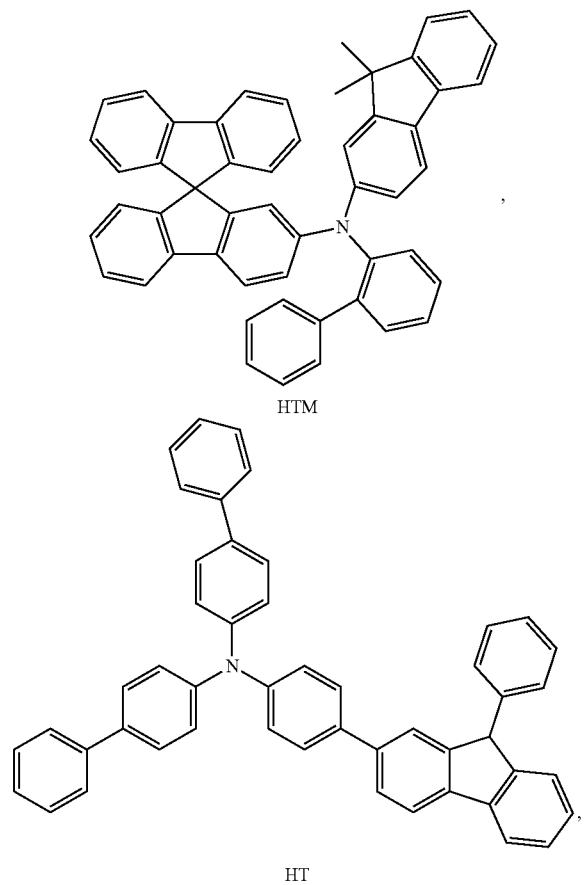

After deposition of each of the above layers, the device was transferred from the deposition chamber into a dry box for encapsulation, and subsequently encapsulated with an UV-curable epoxy and a glass lid containing a moisture getter. The organic electroluminescent device has an emission area of 9 mm².

Preparation Example 1-2 to 1-5: Production of the Organic Electroluminescent Device Except for replacing Compound 2-4 of the electron transport layer in the Preparation example 1-1 with Compound 3-4, 3-7, 3-8 and 3-6 respectively, based on the layer structure of Preparation example 1-1, example 1-2, example 1-3, example 1-4 and example 1-5 were prepared.

Preparation Example 1-1A to 1-1C: Production of the Organic Electroluminescent Device Except for changing the weight ratios of Compound 2-4 and doped Liq of the electron transport layer in the Preparation example 1-1 to be 1:0, 7:3 and 3:7 respectively, based on the layer structure of Preparation example 1-1, example 1-1A, example 1-1B and example 1-1C were prepared.

Preparation Example 1-3A to 1-3C: Production of the Organic Electroluminescent Device Except for changing the weight ratios of Compound 3-7 and doped Liq of the electron transport layer in the Preparation example 1-3 to be 1:0, 7:3 and 3:7 respectively, based on the layer structure of Preparation example 1-3, example 1-3A, example 1-3B and example 1-3C were prepared.

Preparation Example 1-4A: Production of the Organic Electroluminescent Device

Except for changing the weight ratio of Compound 3-8 and doped Liq of the electron transport layer in the Preparation example 1-4 to be 7:3, based on the layer structure of Preparation example 1-4, example 1-4A was prepared.

Preparation Example 1-5A: Production of the Organic Electroluminescent Device

Except for changing the weight ratios of Compound 3-6 and doped quinoline lithium (Liq) of the electron transport layer in the Preparation example 1-5 to be 7:3, based on the layer structure of Preparation example 1-5, example 1-5A was prepared.

Comparative Preparation Example 1: Production of the Organic Electroluminescent Device The organic electroluminescent device was prepared to be similar to the layer structure of Preparation example 1-1, except for replacing Compound 2-4 of the electron transport layer in Preparation example 1-1 with Compound EET09. The Compound EET09 was as described in Japanese Patent Publication No. 2011003793A.

Comparative Preparation Example 2: Production of the Organic Electroluminescent Device The organic electroluminescent device was prepared to be similar to the layer structure of Preparation example 1-1, except for replacing Compound 2-4 of the electron transport layer in Preparation example 1-1 with Compound ETM801. The Compound ETM801 was as described in Japanese Patent No. 6,367,389, and was prepared by e-Ray Optoelectronics Technology.

Test Example 1 to 4

The electroluminescent properties of the organic electroluminescent device made by the above Preparation examples 1-1 to 1-4 were all measured at room temperature, using a constant current source (KEITHLEY 2400 Source Meter, made by Keithley Instruments, Inc., Cleveland, Ohio) and a luminometer (PHOTO RESEARCH SpectraScan PR 650, made by Photo Research, Inc., Chatsworth, Calif.); and its driving voltage ($V_d$), luminous efficiency and value of LT95 at a current density of 50 J were shown in Table 3, wherein LT95 value is defined as the time it takes for the brightness level to fall to a level of 95% relative to the initial brightness as a measure of the usefulness or stability of the organic electroluminescent device.

Comparative Test Example 1

The electroluminescent properties of the organic electroluminescent device made by the Comparative preparation example 1 were measured in the same manner as in the Test example 1.

Test Example 5

The electrical excitation properties of the organic electroluminescent device prepared by the above Preparation examples 1-3 are measured at a current density of 10 mA/cm$^2$ using a constant current source (KEITHLEY 2400 Source Meter, made by Keithley Instruments, Inc., Cleveland, Ohio) and a photometer (PHOTO RESEARCH SpectraScan PR 650, made by Photo Research, Inc., Chatsworth, Calif.), including drive voltage (Vd), luminous efficiency, color coordinates CIE (x, y) and the value of the blue index, recorded in Table 4. The blue light index is the ratio of the luminous efficiency and the color coordinate y. The higher the blue light index is, the better the efficiency of the component is.

Test Example 6

The electroluminescence properties of the organic electroluminescent device made by Preparation example 1-3 were measured in the same manner as in the Test example 5, except that the current density was 50 mA/cm$^2$.

Comparative Test Examples 2 and 3

The organic electroluminescent device prepared by the Comparative preparation example 2 was measured by the measurement method of the Test example 5 at a current density of 10 and 50 mA/cm$^2$ respectively.

Test Examples 7 to 18

The measured values of the organic electroluminescent devices of Preparation examples 1-1, 1-3, 1-4 and 1-6 are listed for the different doping ratios of the electron transport layer and are reported in Table 5.

TABLE 3

| Test example | Preparation example | Electron transport layer compound | $V_d$ (V) | Luminous efficiency (cd/A) | LT95 @ 50J |
|---|---|---|---|---|---|
| Comparative example 1 | Comparative example 1 | EET09:Liq | 3.65 | 9.50 | 20 |
| 1 | 1-1 | Compound 2-4:Liq | 4.71 | 9.35 | 28 |
| 2 | 1-2 | Compound 3-4:Liq | 3.75 | 10.00 | — |
| 3 | 1-3 | Compound 3-7:Liq | 4.09 | 9.44 | 152 |
| 4 | 1-4 | Compound 3-8:Liq | 3.86 | 9.00 | 24 |

TABLE 4

| Test example | Preparation example | Cutrent density (mA/cm²) | Election transpon layer command | $V_d$ (V) | Lumincus efficiency (cd/A) | CIE-y | Blue light index |
|---|---|---|---|---|---|---|---|
| Comparative example 2 | Comparative example 2 | 10 | ETM801:Liq | 4.21 | 8.54 | 0.142 | 60.06 |
| 5 | 1-3 | | Compound 3-7:Liq | 4.15 | 8.90 | 0.138 | 64.54 |
| Comparative example 3 | Comparative example 2 | 50 | ETM801:Liq | 5.50 | 8.09 | 0.139 | 58.03 |
| 6 | 1-3 | | Compound 3-7:Liq | 5.25 | 7.80 | 0.135 | 57.95 |

TABLE 5

| Test example | Preparation example | Electron transport layer compound | Doping ratio | $V_d$ | Luminous efficiency (cd/A) | CIE-y | Blue light index |
|---|---|---|---|---|---|---|---|
| 7 | 1-1 | Compound 2-4:Liq | 5:5 | 4.67 | 9.35 | 0.13 | 71.98 |
| 8 | 1-1A | | 1:0 | 5.89 | 8.69 | 0.135 | 64.28 |
| 9 | 1-1B | | 7:3 | 4.84 | 9.66 | 0.132 | 73.46 |
| 10 | 1-1C | | 3:7 | 5.13 | 7.81 | 0.128 | 60.87 |
| 11 | 1-3 | Compound 3-7:Liq | 5:5 | 4.02 | 9.43 | 0.135 | 69.75 |
| 12 | 1-3A | | 1:0 | 4.2 | 6.28 | 0.147 | 42.72 |
| 13 | 1-3B | | 7:3 | 4.02 | 8.83 | 0.15 | 58.98 |
| 14 | 1-3C | | 3:7 | 4.4 | 8.52 | 0.132 | 64.35 |
| 15 | 1-4 | Compound 3-8:Liq | 5:5 | 3.83 | 8.5 | 0.132 | 64.59 |
| 16 | 1-4A | | 7:3 | 3.73 | 8.02 | 0.131 | 61.31 |
| 17 | 1-6 | Compound 3-6:Liq | 5:5 | 4.62 | 7.38 | 0.13 | 5.74 |
| 18 | 1-6A | | 7:3 | 4.1 | 7.93 | 0.13 | 60.81 |

Preparation Example 2-1: Production of the Organic Electroluminescent Device

Prior to being loaded into an evaporation system, a substrate was cleaned and then degreased with a solvent and UV ozone. The substrate was then transferred into a vacuum deposition chamber for deposition of all layers on top of the substrate. By evaporation on a heated boat under a vacuum of about $10^{-6}$ Torr, each of the layers was deposited in sequence as shown in FIG. 3:

a) a hole injection layer, having a thickness of 20 nm, comprising HTM doped with a P-type electrically conductive dopant of 6% by weight, wherein the P-type electrically conductive dopant is purchased from Shanghai Yufeng Chemical Co., Ltd., and HTM is purchased from Merck & Co., Inc.;

b) a hole transport layer, having a thickness of 150 nm, HTM;

c) an exciton blocking layer, having a thickness of 10 nm, HT (prepared by e-Ray Optoelectronics Technology);

d) a light emitting layer, having a thickness of 25 nm, comprising EBH doped with 4% by weight of BD, wherein BD and EBH are prepared by e-Ray Optoelectronics Technology; e) a hole blocking layer, having a thickness of 5 nm, Compound 2-4;

f) an electron transport layer, having a thickness of 20 nm, containing Compound 2-4 and doped lithium quinolate (Liq), and a weight ratio is 5:5;

g) an electron injection layer, having a thickness of 1.5 nm, Liq; and h) a cathode, having a thickness of approximately 180 nm, containing aluminum (Al).

The device structure of Preparation example 1 may be denoted as ITO/HTM: P-type electrically conductive dopant (20 nm)/HTM (150 nm)/HT (10 nm)/EBH: BD (25 nm)/Compound 2-4 (5 nm)/Compound 2-4: Liq (20 nm)/Liq (1.5 nm)/Al (180 nm).

After deposition of each of the above layers, the device was transferred from the deposition chamber into a dry box for encapsulation, and subsequently encapsulated with an UV-curable epoxy and a glass lid containing a moisture getter. The organic electroluminescent device has an emission area of 9 mm².

Preparation Example 2-2: Production of the Organic Electroluminescent Device Except for changing the weight ratios of Compound 2-4 of the hole blocking layer and the electron transport layer in the Preparation example 2-1 to be Compound 3-7, based on the layer structure of Preparation example 1-1, Preparation example 2-2 was prepared.

Preparation Example 2-1A to 2-1B: Production of the Organic Electroluminescent Device Except for changing the weight ratios of Compound 2-4 and doped Liq of the electron transport layer in the Preparation example 2-1 to be 7:3 and 3:7 respectively, based on the layer structure of Preparation example 2-1, Preparation example 2-1A and Preparation example 2-1B were prepared.

Preparation Example 2-2A to 2-2B: Production of the Organic Electroluminescent Device Except for changing the weight ratios of Compound 3-7 and doped Liq of the electron transport layer in the Preparation example 2-2 to be 7:3 and 3:7 respectively, based on the layer structure of Preparation example 2-2, Preparation example 2-2A and Preparation example 2-2B were prepared.

Comparative Preparation Example 3: Production of the Organic Electroluminescent Device The organic electroluminescent device was prepared to be similar to the layer structure of Preparation example 2-1, except for replacing Compound 2-4 of the hole blocking layer and the electron transport layer in Preparation example 2-1 with Compound EET09 respectively.

Test Example 19 to 24

The electroluminescent properties of the organic electroluminescent device prepared by the above Preparation examples 2-1 to 2-2 were measured by the measurement method that is identical to Test example 7, and are recorded in Table 6.

Comparative Test Example 4

The electroluminescent properties of the organic electroluminescent device made by the Comparative preparation example 4 were measured by the measurement method identical to Test example 19 and recorded in Table 6.

As described above, the organic electroluminescent device containing the phenyl biphenylpyrimidine compound of formula (I) of the present disclosure exhibits good heat resistance and remarkably improves its lifetime. Therefore, the organic electroluminescent device of the present disclosure can meet various application requirements, having a very high technical value.

The above embodiments are merely illustrative and are not intended to limit the disclosure. Modifications and variations of the above described embodiments can be made by one skilled in the art without departing from the spirit and scope of the disclosure. Therefore, the scope of the disclosure is defined by the scope of the appended claims. As long as the effects and implementation purposes of the present disclosure are not affected, they should be encompassed in this technical disclosure.

The invention claimed is:

1. A phenyl biphenylpyrimidine compound of formula (I):

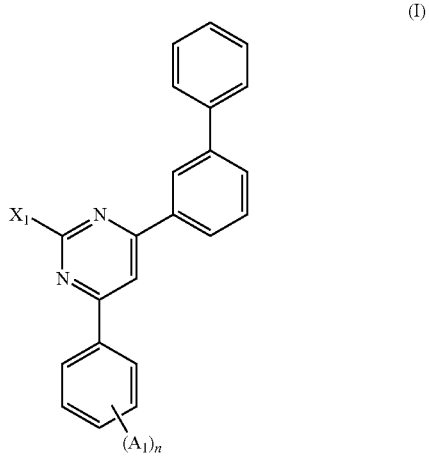

wherein:

$X_1$ represents one selected from the group consisting of unsubstituted pyridyl, and phenyl substituted with $C_{1-4}$ alkyl;

TABLE 6

| Test example | Preparation example | Hole blocking layer compound | Electron transport layer compound | Doping ratio | $V_d$ | Lumincus efficiency (cd/A) | CIE-y | Blue light index |
|---|---|---|---|---|---|---|---|---|
| Comparative example 4 | Comparative example 3 | EET09 | EET09:Liq | 5:5 | 3.46 | 8.81 | 0.129 | 68.4 |
| 19 | 2-1 | Compound 2-4 | Compound 2-4:Liq | 5:5 | 4.1 | 8.66 | 0.134 | 64.72 |
| 20 | 2-1A | | | 7:3 | 4.17 | 8.88 | 0.144 | 61.84 |
| 21 | 2-1B | | | 3:7 | 4.51 | 8.76 | 0.133 | 65.67 |
| 22 | 2-2 | Compound 3-7 | Compound 3-7:Liq | 5:5 | 3.8 | 9.12 | 0.127 | 71.81 |
| 23 | 2-2A | | | 7:3 | 4.99 | 9.69 | 0.132 | 73.52 |
| 24 | 2-2B | | | 3:7 | 5.43 | 7.48 | 0.129 | 57.94 |

$A_1$ represents one selected from the group consisting of:

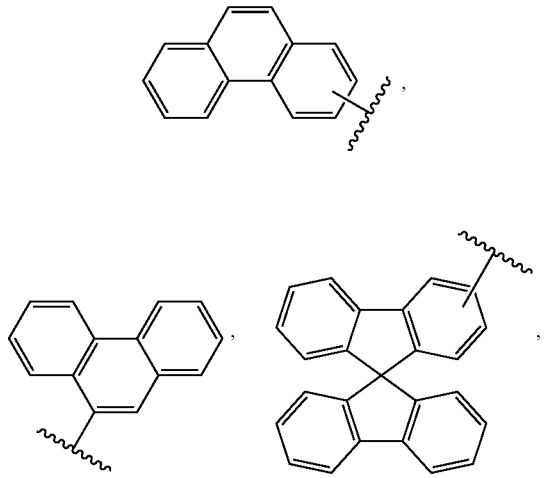

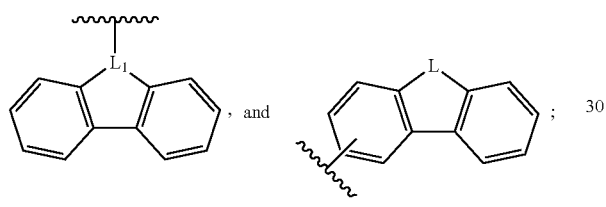

wherein

L represents N, N-$R_1$, O or S, and $R_1$ is unsubstituted $C_{6-18}$ aryl; and $L_1$ represents N or N-$R_2$, and $R_2$ is unsubstituted $C_{6-18}$ arylene attached to the compound of formula (I); and n represents an integer of 1 or 2, wherein when n represents 2, each $A_1$ is the same or different.

2. The phenyl biphenylpyrimidine compound of formula (I) of claim 1, which is one selected from the group consisting of:

(1-3)

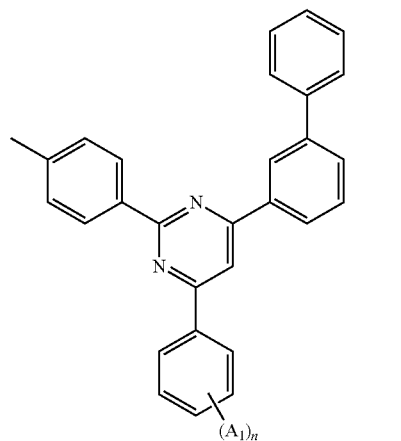

-continued (1-4)

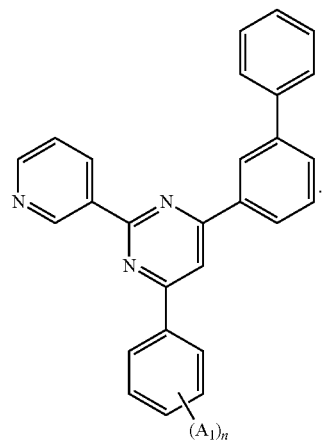

3. The phenyl biphenylpyrimidine compound of formula (I) of claim 1, which is represented by formula (1-5) or formula (1-6) below when n is 1:

(1-5)

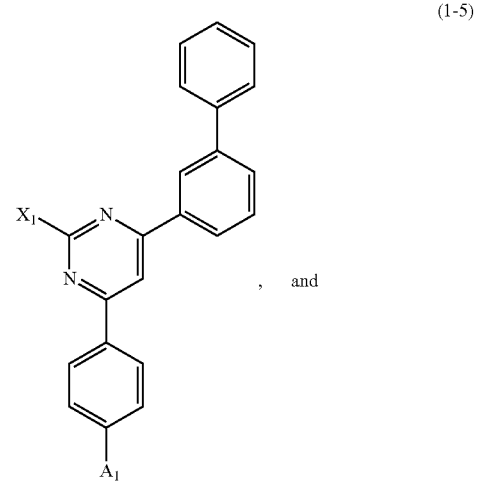

, and (1-6)

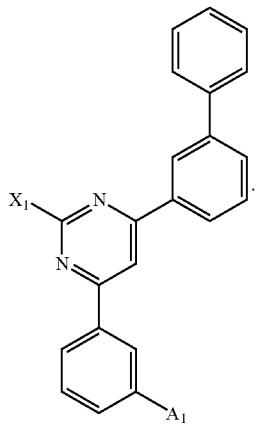

4. The phenyl biphenylpyrimidine compound of formula (I) of claim 1, which is one selected from the group consisting of:
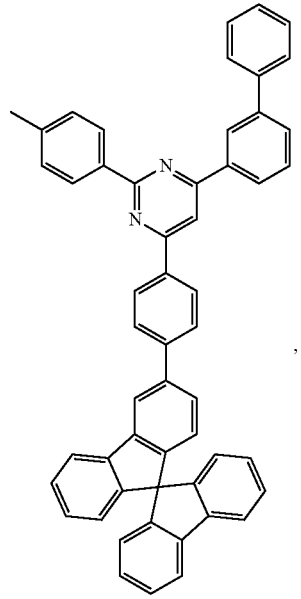
(2-4)
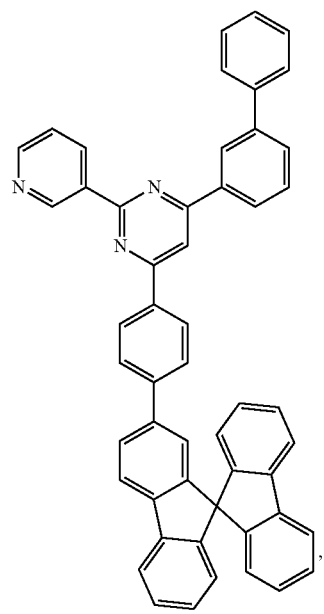
(3-5)
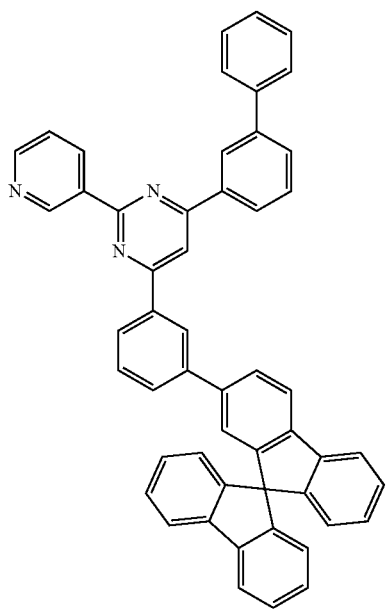
(3-4)
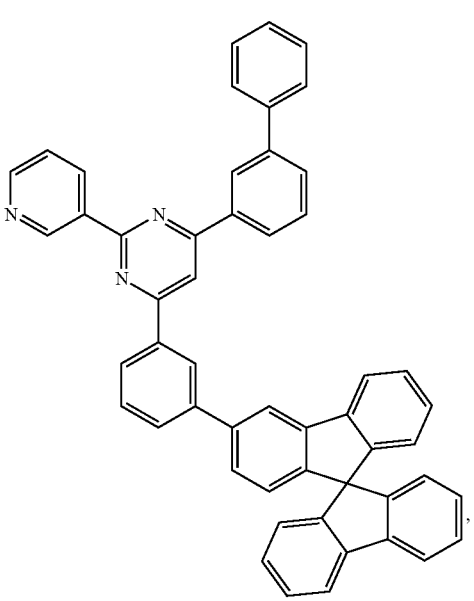
(3-6)

-continued (3-7)
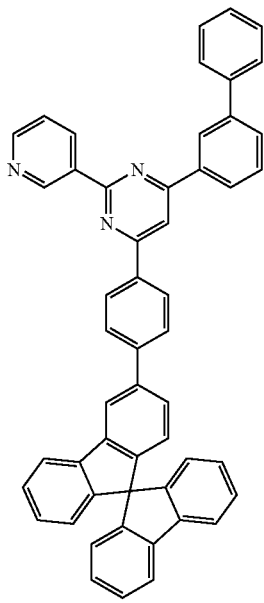
and (3-8)
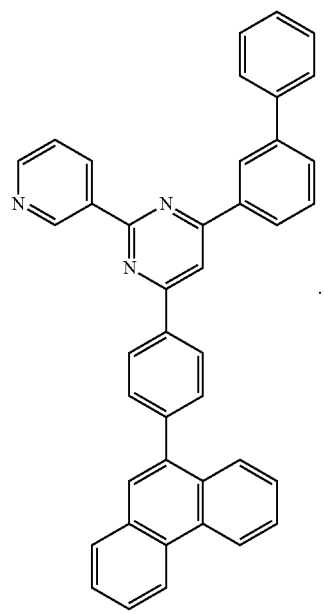

5. The phenyl biphenylpyrimidine compound of formula (I) of claim 1, which is represented by formula (1-7) below when n is 2:

(1-7)
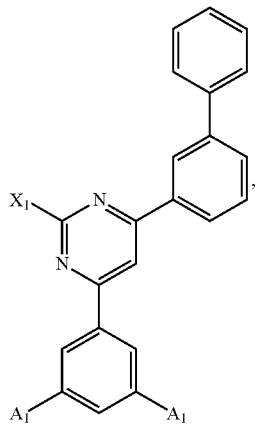

wherein each $A_1$ is the same or different.

6. An organic electroluminescent device, comprising:
a cathode;
an anode; and
an organic layer between the cathode and the anode, the organic layer comprising the phenyl biphenylpyrimidine compound of formula (I) of claim 1.

7. The organic electroluminescent device of claim 6, wherein the organic layer is an electron transport layer.

8. The organic electroluminescent device of claim 7, wherein the electron transport layer has a thickness of 20 nm to 30 nm.

9. The organic electroluminescent device of claim 7, wherein the electron transport layer further comprises an N-type electrically conductive dopant.

10. The organic electroluminescent device of claim 9, wherein the N-type electrically conductive dopant is in an amount of more than 0% by weight up to 50% by weight.

11. The organic electroluminescent device of claim 9, wherein the N-type electrically conductive dopant is lithium quinolate.

12. The organic electroluminescent device of claim 7, wherein the organic layer further comprises a hole blocking layer.

13. The organic electroluminescent device of claim 12, wherein the hole blocking layer has a thickness of more than 0 nm up to 5 nm.

* * * * *